(12) United States Patent
Wu et al.

(10) Patent No.: US 10,322,408 B2
(45) Date of Patent: Jun. 18, 2019

(54) METHOD FOR DEGRADING AN ORGANIC MATERIAL AND METHOD FOR STERILIZING

(71) Applicant: NATIONAL TSING HUA UNIVERSITY, Hsinchu (TW)

(72) Inventors: Jyh-Ming Wu, Hsinchu County (TW); Wei-En Chang, Miaoli County (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 105 days.

(21) Appl. No.: 15/787,721

(22) Filed: Oct. 19, 2017

(65) Prior Publication Data

US 2018/0036719 A1 Feb. 8, 2018

Related U.S. Application Data

(62) Division of application No. 15/163,696, filed on May 25, 2016, now abandoned.

(30) Foreign Application Priority Data

Jan. 27, 2016 (TW) .............................. 105102523 A

(51) Int. Cl.
C02F 1/32 (2006.01)
B01J 27/051 (2006.01)
(Continued)

(52) U.S. Cl.
CPC ............ *B01J 27/051* (2013.01); *A61L 2/238* (2013.01); *A61L 9/01* (2013.01); *A61L 9/22* (2013.01); *B01J 35/004* (2013.01); *B01J 35/0013* (2013.01); *B01J 35/023* (2013.01); *B01J 35/026* (2013.01); *B01J 37/04* (2013.01); *B01J 37/10* (2013.01); *C01G 39/06* (2013.01); *C02F 1/50* (2013.01); *C02F 1/725* (2013.01); *B01J 35/002* (2013.01); *C01P 2002/20* (2013.01);
(Continued)

(58) Field of Classification Search
CPC . B01J 27/051; B01J 35/02; B01J 37/04; B01J 37/10; A61L 9/22; C01G 39/06; C02F 1/50; C02F 1/72
See application file for complete search history.

(56) References Cited

U.S. PATENT DOCUMENTS

2012/0272869 A1* 11/2012 Shaw ...................... C01G 39/06
106/287.18
2013/0082009 A1* 4/2013 O'Keefe ................ B01J 23/002
210/748.14

OTHER PUBLICATIONS

CN-102794190-A, Nov. 2012, Qingsi Wang; B01J27/25 (Year: 2012).*

* cited by examiner

*Primary Examiner* — Walter D. Griffin
*Assistant Examiner* — Cameron J Allen
(74) *Attorney, Agent, or Firm* — CKC & Partners Co., LLC

(57) ABSTRACT

A method for manufacturing a molybdenum disulfide powder includes conducting a precursor solution preparation step and a hydrothermal synthesis step. The precursor solution preparation step includes providing sodium molybdenum oxide dihydrate and thiourea, and conducting a mixing step. In the mixing step, an acid solution is mixed with the sodium molybdenum oxide dihydrate and the thiourea by titrating so as to form a precursor solution. In the hydrothermal synthesis step, the precursor solution is put into a hydrothermal container for reacting at a temperature ranging from 100° C. to 350° C. for 8 hours to 40 hours, thus the molybdenum disulfide powder is formed.

8 Claims, 25 Drawing Sheets

(51) Int. Cl.

| | | |
|---|---|---|
| *A61L 9/22* | (2006.01) | |
| *B01J 35/02* | (2006.01) | |
| *B01J 37/04* | (2006.01) | |
| *B01J 37/10* | (2006.01) | |
| *C01G 39/06* | (2006.01) | |
| *C02F 1/50* | (2006.01) | |
| *C02F 1/72* | (2006.01) | |
| *A61L 2/238* | (2006.01) | |
| *A61L 9/01* | (2006.01) | |
| *B01J 35/00* | (2006.01) | |
| *C02F 1/36* | (2006.01) | |
| *C02F 101/30* | (2006.01) | |

(52) U.S. Cl.
CPC ...... *C01P 2002/72* (2013.01); *C01P 2004/03* (2013.01); *C01P 2004/04* (2013.01); *C01P 2004/62* (2013.01); *C02F 1/36* (2013.01); *C02F 2101/308* (2013.01); *C02F 2303/04* (2013.01); *C02F 2305/023* (2013.01); *C02F 2305/10* (2013.01)

110 sodium molybdenum oxide dihydrate and thiourea are provided — 111 a mixing step is conducted — 112

500 a molybdenum disulfide powder is provided — 510 a contacting step is conducted — 520 a sterilizing step is conducted — 530

METHOD FOR DEGRADING AN ORGANIC MATERIAL AND METHOD FOR STERILIZING

RELATED APPLICATIONS

The present application is a divisional application of the U.S. application Ser. No. 15/163,696, filed on May 25, 2016, which claims priority to Taiwan Application Serial Number 105102523, filed on Jan. 27, 2016, the entire contents of which are herein incorporated by reference.

BACKGROUND

Technical Field

The present disclosure relates to a molybdenum disulfide powder, a method for manufacturing the same, a method for degrading an organic material using the same, and a method for sterilizing using the same. More particularly, the present disclosure relates to a molybdenum disulfide powder with catalytic activity, a method for manufacturing the same, a method for degrading an organic material using the same, and a method for sterilizing using the same.

Description of Related Art

A photocatalyst is a substance which can accelerate a chemical reaction after irradiated with light. The common photocatalysts include gallium phosphide (GaP), gallium arsenide (GaAs), cadmium sulfide (CdS), stannic oxide ($SnO_2$), zinc oxide (ZnO), titanium dioxide ($TiO_2$), and so on. The photocatalyst can generate a plurality of electron-hole pairs after irradiated with light, in which the holes have oxidation ability and the electrons have reduction ability. The holes and the electrons can react with water molecules and oxygen molecules on a surface of the photocatalyst so as to generate hydroxyl radicals (OH.) and superoxide ions ($O_2^-$). The hydroxyl radicals have strong oxidation ability, the superoxide ions have strong reduction ability. By redox reactions, the photocatalyst can spoil cell membranes so as to achieve the sterilizing effect or can degrade organic gases or organic materials into water and carbon dioxide. Accordingly, a deodorization effect and a water purification effect can be achieved. The reaction between the holes and the water molecules and the reaction between the electrons and the oxygen molecules can be illustrated by Equation (1), Equation (2) and Equation (3):

$$h_{VB}^+ + H_2O \rightarrow H^+ + OH. \qquad (1);$$

$$h_{VB}^+ + OH^- \rightarrow OH. \qquad (2); \text{ and}$$

$$e_{CB}^- + O_2 \rightarrow O_2^- \qquad (3).$$

The photocatalysts can use the sun light to induce the catalytic activity thereof and cause no secondary pollution, so draw a lot of attention. Among the photocatalysts, the titanium dioxide has a relatively stronger redox ability after irradiated with ultraviolet (UV) light and a stable chemical property. Furthermore, the titanium dioxide is harmless to the environment, and the material cost thereof is low. Accordingly, the titanium dioxide is becoming the mainstream material in the field of photocatalysts.

However, the catalytic activity of the photocatalyst is induced only when a certain energy is provided. Take the titanium dioxide for example, an energy greater than 3.2 eV (electronvolt) is required to induce the catalytic activity thereof, which is equivalent to an UV light with a wavelength lower than 387.5 nm. Although the sun light includes the UV light with the wavelength lower than 387.5 nm, the ratio of the UV light in the sun light is low. Therefore, the sun light cannot completely induce the catalytic activity of the titanium dioxide.

For solving the foregoing problem, a product equipped with an UV lamp is provided, whereby the photocatalyst is directly irradiated with the UV light for effectively enhancing the catalytic activity thereof. However, the UV light with a shorter wavelength is harmful to human body, so only can be used under certain conditions or environments, which is quite limited in use. Moreover, replacing the sun light with the UV lamp, an extra energy consumption is increased, which does not meet the demands of environmental protection and increases the cost.

To sum up, how to develop a new catalyst material, which does not rely on the irradiation of light with short wavelength and can provide desired catalytic activity, and can accordingly reduce energy consumption and cost, and meet the demands of environmental protection, is the goal of the related academia and industries.

SUMMARY

According to one aspect of the present disclosure, a method for manufacturing a molybdenum disulfide powder includes steps as follows. A precursor solution preparation step is conducted, and a hydrothermal synthesis step is conducted. The precursor solution preparation step includes steps as follows. Sodium molybdenum oxide dihydrate and thiourea are provided, and a mixing step is conducted. In the mixing step, an acid solution is mixed with the sodium molybdenum oxide dihydrate and the thiourea by titrating so as to form a precursor solution. In the hydrothermal synthesis step, the precursor solution is put into a hydrothermal container for reacting at a temperature ranging from 100° C. to 350° C. for 8 hours to 40 hours, thus the molybdenum disulfide powder is formed.

According to another aspect of the present disclosure, a molybdenum disulfide powder is provided. The molybdenum disulfide powder is made by the method according to the foregoing aspect, and the molybdenum disulfide powder is stacked from a plurality of layered structures.

According to yet another aspect of the present disclosure, a method for degrading an organic material includes steps as follows. A molybdenum disulfide powder is provided, a contacting step is conducted, and a degrading step is conducted. The molybdenum disulfide powder is stacked from a plurality of layered structures, and at least one of the layered structures is an odd-layer structure. In the contacting step, the molybdenum disulfide powder is contacted with a medium, and the medium includes at least one organic material and water. In the degrading step, a mechanical perturbation is generated in the medium to polarize the molybdenum disulfide powder, and a pair of electron and hole are generated for degrading the organic material.

According to further another aspect of the present disclosure, a method for sterilizing includes steps as follows. A molybdenum disulfide powder is provided, a contacting step is conducted, and a sterilizing step is conducted. The molybdenum disulfide powder is stacked from a plurality of layered structures, and at least one of the layered structures is an odd-layer structure. In the contacting step, the molybdenum disulfide powder is contacted with a medium, and the medium includes at least one bacterium and water. In the sterilizing step, a mechanical perturbation is generated in the medium to polarize the molybdenum disulfide powder, and a pair of electron and hole are generated for killing the bacterium.

BRIEF DESCRIPTION OF THE DRAWINGS

The present disclosure can be more fully understood by reading the following detailed description of the embodiment, with reference made to the accompanying drawings as follows.

DETAILED DESCRIPTION

Method for Manufacturing Molybdenum Disulfide Powder

Figure 1:
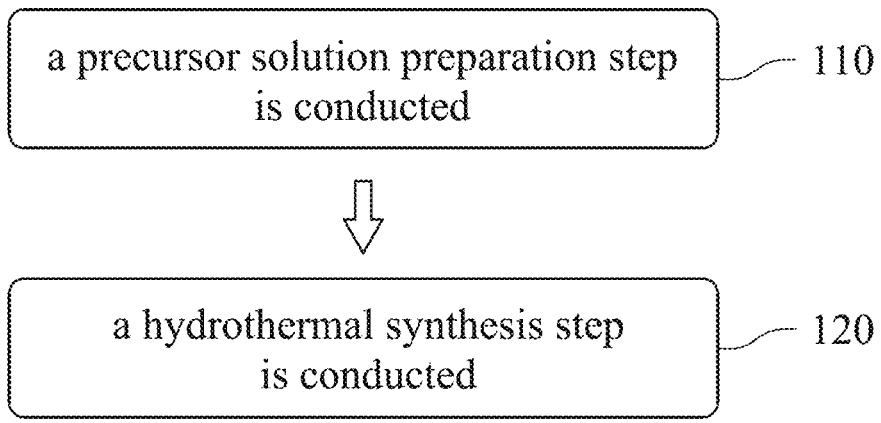
FIG. 1 is a flow diagram showing a method for manufacturing a molybdenum disulfide powder according to one embodiment of the present disclosure.

FIG. 1 is a flow diagram showing a method for manufacturing a molybdenum disulfide powder 100 according to one embodiment of the present disclosure. In FIG. 1, the method for manufacturing the molybdenum disulfide powder 100 includes Step 110 and Step 120.

Figure 2:
FIG. 2 is a flow diagram showing Step 110 in FIG. 1.

In Step 110, a precursor solution preparation step is conducted. Please refer to FIG. 2 at the same time. FIG. 2 is a flow diagram showing Step 110 in FIG. 1. Step 110 includes Step 111 and Step 112.

In Step 111, sodium molybdenum oxide dihydrate and thiourea are provided. A mole ratio of the sodium molybdenum oxide dihydrate to the thiourea can range from 1:0.5 to 1:5.

In Step 112, a mixing step is conducted, in which an acid solution is mixed with the sodium molybdenum oxide dihydrate and the thiourea by titrating so as to form a precursor solution, whereby it is favorable to conduct a reaction in a following hydrothermal synthesis step. According to one example of the present disclosure, an acid is mixed with deionized water to form the acid solution, and then the acid solution is titrated into a container having the sodium molybdenum oxide dihydrate and the thiourea. The acid is added for lowering a pH value of the precursor solution. The acid can be but is not limited to sulfuric acid, hydrochloric acid, nitric acid and acetic acid. The acid solution can be mixed with the sodium molybdenum oxide dihydrate and the thiourea with a titrating rate which is greater than 0 ml/min and is smaller than or equal to 2.03 ml/min. When the titrating rate is too fast, the molybdenum disulfide powder tends to agglomerate, which is unfavorable to form the molybdenum disulfide powder stacked from layered structures with fewer layers.

Figure 3:
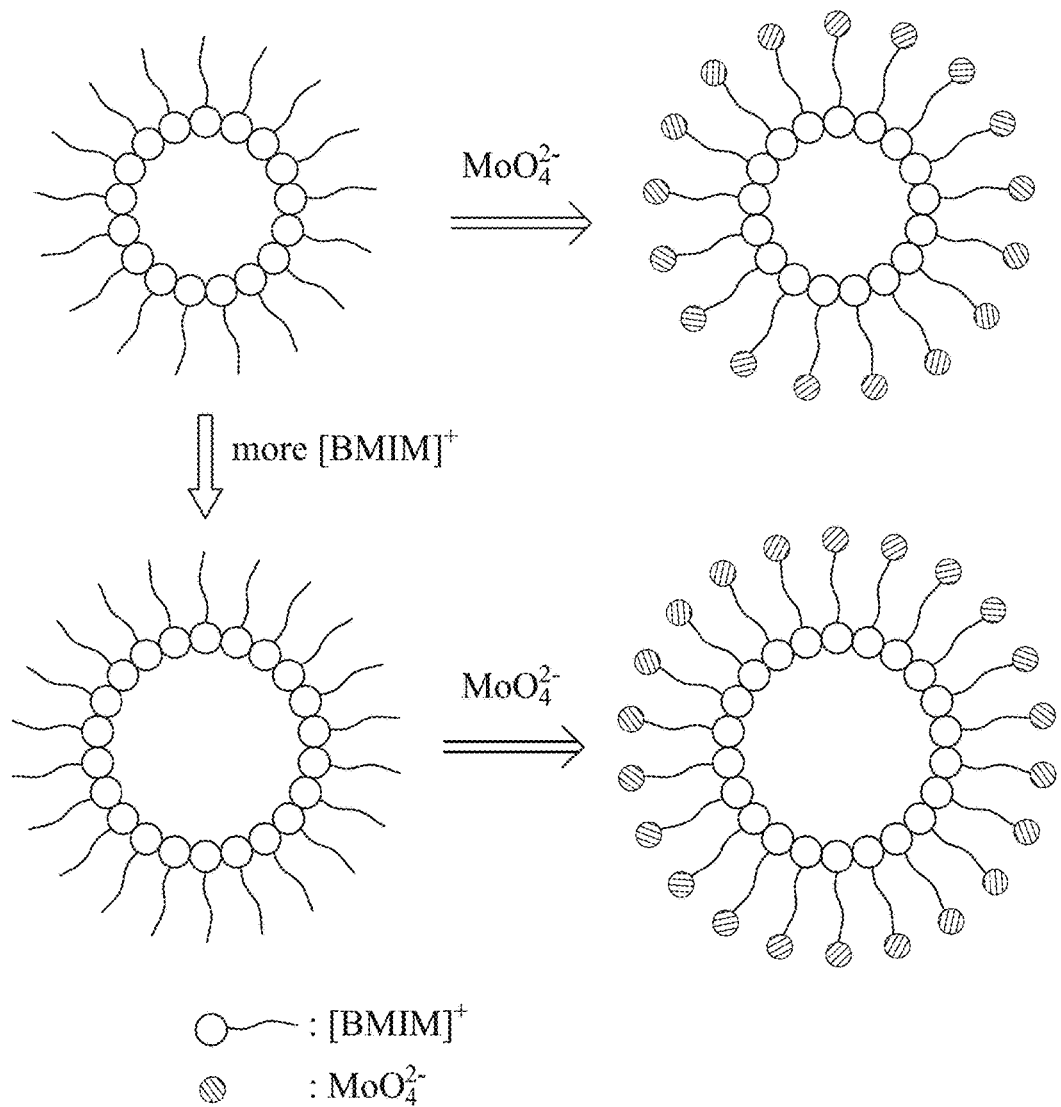
FIG. 3 is a schematic view showing a nucleation space provided by [BMIM]$^+$.

According to one example of the present disclosure, the precursor solution preparation step further includes providing a solution of 1-butyl-3-methylimidazolium chloride salt ([BMIM][Cl]) before conducting the mixing step. In other words, the solution of the [BMIM][Cl] is first mixed with the sodium molybdenum oxide dihydrate and the thiourea, and then the mixing step is conducted. A molar concentration of the [BMIM][Cl] in the precursor solution is greater than 0 M, and is smaller than or equal to 5M. When the molar concentration of the [BMIM][Cl] in the precursor solution is greater than 0 M, it is favorable the molybdenum disulfide powder to form a nanoflower structure stacked from layered structures. When the molar concentration of the [BMIM][Cl] in the precursor solution is smaller than or equal to 5M, an excessively large particle size of the nanoflower structure of the molybdenum disulfide powder can be prevented (i.e., an excessively large particle size of the molybdenum disulfide powder can be prevented). Accordingly, an excessive small specific surface area can be prevented. FIG. 3 is a schematic view showing a nucleation space provided by [BMIM]$^+$. In FIG. 3, the [BMIM][Cl] dissociates into [BMIM]$^+$ and Cl$^-$ (not shown) in deionized water. The [BMIM]$^+$ forms a vesicle in the deionized water due to a hydrophobia thereof, and the MoO$_4^{2-}$ is absorbed on the [BMIM]$^+$ due to the attraction between the positive charge and the negative charge, which is favorable to form the nanoflower structure stacked from layered structures. When the molar concentration of the [BMIM][Cl] is increased, a radius of the vesicle formed from the [BMIM]$^+$ is increased as shown in the lower portion of FIG. 3. It can be concluded from FIG. 3 that the molar concentration of the [BMIM][Cl] can be adjusted according to practical needs so as to adjust the particle size of the molybdenum disulfide powder.

Please refer back to FIG. 1. In Step 120, the hydrothermal synthesis step is conducted, in which the precursor solution is put into a hydrothermal container for reacting at a temperature ranging from 100° C. to 350° C. for 8 hours to 40 hours, thus the molybdenum disulfide powder is formed. According to one example of the present disclosure, the hydrothermal container can be made of teflon, and the hydrothermal synthesis step can be conducted at a temperature of 220° C. for 24 hours. A reaction equation of Step 120 is as follows:

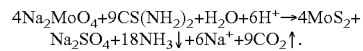

Figure 4:
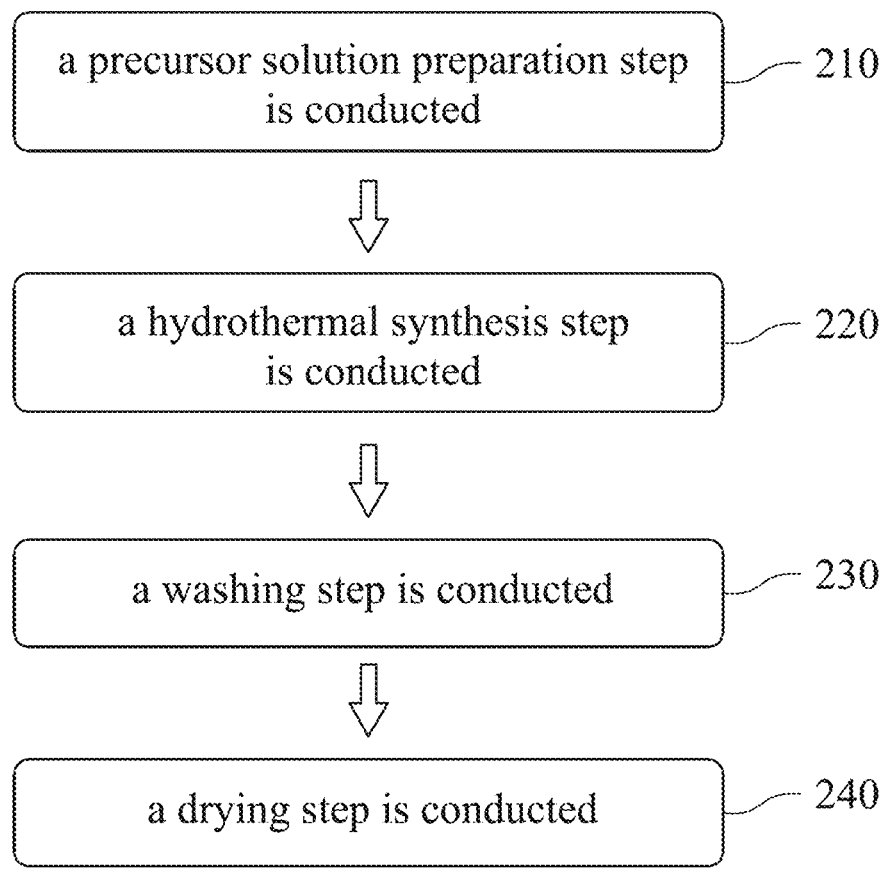
FIG. 4 is a flow diagram showing a method for manufacturing a molybdenum disulfide powder according to another embodiment of the present disclosure.

FIG. 4 is a flow diagram showing a method for manufacturing a molybdenum disulfide powder 200 according to another embodiment of the present disclosure. In FIG. 4, the method for manufacturing the molybdenum disulfide powder 200 includes Step 210, Step 220, Step 230 and Step 240.

In Step 210, a precursor solution preparation step is conducted. In Step 220, a hydrothermal synthesis step is conducted. The details of Step 210 and Step 220 can be the same as that of Step 110 and Step 120 in FIG. 1, and will not be repeated herein.

In Step 230, a washing step is conducted, in which the molybdenum disulfide powder is first washed with deionized water and then washed with ethanol. According to one example of the present disclosure, the molybdenum disulfide powder can be first washed with deionized water for several times for preferably cleaning other chemical substances on the surface thereof. Then the molybdenum disulfide powder is washed with ethanol for rapid drying.

In Step 240, a drying step is conducted, in which the molybdenum disulfide powder dealt with the washing step is heated to dryness. The drying step is for removing the moisture remained in the molybdenum disulfide powder. The drying step can be conducted at a temperature ranging from 40° C. to 100° C. for 8 hours to 24 hours.

EXAMPLES AND COMPARATIVE EXAMPLES

The first example: sodium molybdenum oxide dihydrate (0.002976 mole) and thiourea (0.009065 mole) are put into a beaker. Deionized water (60 ml) and hydrochloric acid (1 ml, 12 M) are mixed so as to form an acid solution. The acid solution is titrated into the beaker containing the sodium molybdenum oxide dihydrate and the thiourea in 30 minutes, then is stirred with magnet stirrer for 10 minutes, so that a precursor solution is obtained. Afterwards, the precursor solution is put into a hydrothermal container made of teflon and then put into an oven maintained at a temperature of 220° C. for 24 hours. Let the hydrothermal container stand still until the temperature thereof is reduced to the room temperature. The suspension in the hydrothermal container is centrifuged at 5,500 rpm for collecting a precipitation. Then the precipitation is washed with deionized water and then collected by centrifugation at 5,500 rpm, which is repeated four times. Then the precipitation is washed with ethanol and then collected by centrifugation at 5,500 rpm. The precipitation is put into the oven and is heated at 50° C. for 12 hours. Thus, the molybdenum disulfide powder of the first example is obtained. The molybdenum disulfide powder is black, and a mass thereof is about 4 g.

The second example: sodium molybdenum oxide dihydrate (0.002976 mole) and thiourea (0.009065 mole) are put into a beaker, then a solution of [BMIM][Cl] (1 ml, 1 M) is put into the beaker. The solution of [BMIM][Cl] is mixed with the sodium molybdenum oxide dihydrate and the thiourea. Deionized water (59 ml) and hydrochloric acid (1 ml, 12 M) are mixed so as to form an acid solution. The acid solution is titrated into the beaker containing the sodium molybdenum oxide dihydrate and the thiourea in 30 minutes, then is stirred with magnet stirrer for 10 minutes, so that a precursor solution is obtained. The following steps are the same as that in the first example, and will not repeated herein.

The third example: sodium molybdenum oxide dihydrate (0.002976 mole) and thiourea (0.009065 mole) are put into a beaker, then a solution of [BMIM][Cl] (5 ml, 1 M) is put into the beaker. The solution of [BMIM][Cl] is mixed with the sodium molybdenum oxide dihydrate and the thiourea. Deionized water (55 ml) and hydrochloric acid (1 ml, 12 M) are mixed so as to form an acid solution. The acid solution is titrated into the beaker containing the sodium molybdenum oxide dihydrate and the thiourea in 30 minutes, then is stirred with magnet stirrer for 10 minutes, so that a precursor solution is obtained. The following steps are the same as that in the first example, and will not repeated herein.

The fourth example: sodium molybdenum oxide dihydrate (0.002976 mole) and thiourea (0.009065 mole) are put into a beaker, then a solution of [BMIM][Cl] (10 ml, 1 M) is put into the beaker. The solution of [BMIM][Cl] is mixed with the sodium molybdenum oxide dihydrate and the thiourea. Deionized water (50 ml) and hydrochloric acid (1 ml, 12 M) are mixed so as to form an acid solution. The acid solution is titrated into the beaker containing the sodium molybdenum oxide dihydrate and the thiourea in 30 minutes, then is stirred with magnet stirrer for 10 minutes, so that a precursor solution is obtained. The following steps are the same as that in the first example, and will not repeated herein.

The first comparative example: a commercial available molybdenum disulfide powder (purchased from Sigma Aldrich Corporation) has a particle size smaller than 2 μm.

The second comparative example: sodium molybdenum oxide dihydrate (0.002976 mole) and thiourea (0.009065 mole) are dissolved with deionized water (60 ml), then is stirred with magnet stirrer until a clear and transparent solution is obtained. Then hydrochloric acid (1 ml, 12 M) contained in a dropper is titrated into the solution with a titrating rate of 6 ml/min, then is stirred with magnet stirrer for 10 minutes, so that a precursor solution is obtained. The following steps are the same as that in the first example, and will not repeated herein.

The third comparative example: a rhodamine solution has a concentration of 10 ppm.

The fourth comparative example: a commercial available titanium dioxide powder (purchased from Sigma Aldrich Corporation) has an average particle size of 21 nm, and a specific surface area ranging from 35 $m^2$/g to 65 $m^2$/g.

Molybdenum Disulfide Powder

Results of SEM and TEM: a cold field emission SEM (Hitachi SU8010) is used to observe the surface morphology of the molybdenum disulfide powder of the first example to the fourth example at 10 k magnification and at 50 k magnification with an accelerating voltage of 10 kV. A high resolution TEM (JEOL JEM-3000F) is used to observe the arrangement of atoms, the crystalline property and the selected area diffraction (SAD) pattern of the molybdenum disulfide powder of the first example to the fourth example.

Figure 5A:
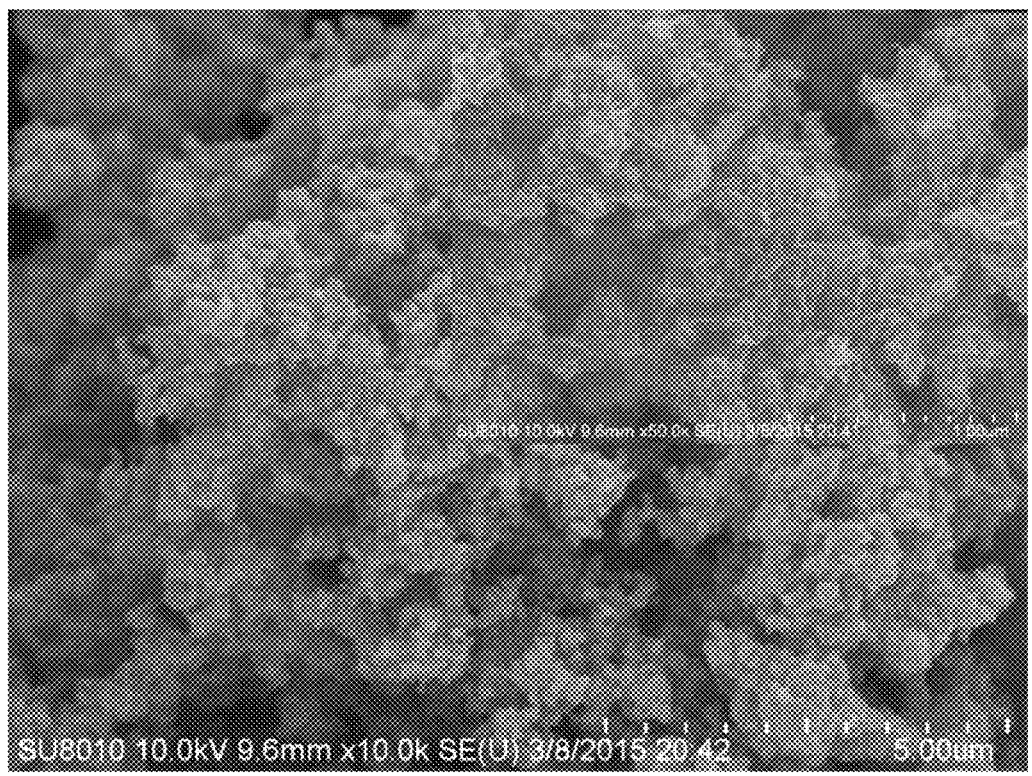
FIG. 5A are scanning electron microscope (SEM) images of a molybdenum disulfide powder according to the first example of the present disclosure.
Figure 5B:
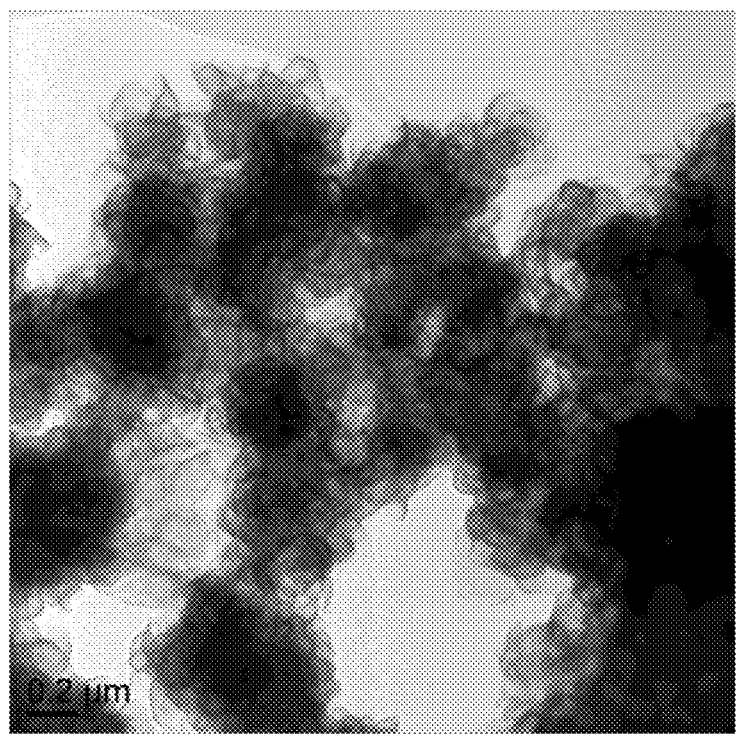
FIG. 5B is a transmission electron microscope (TEM) image of the molybdenum disulfide powder according to the first example of the present disclosure.
Figure 5C:
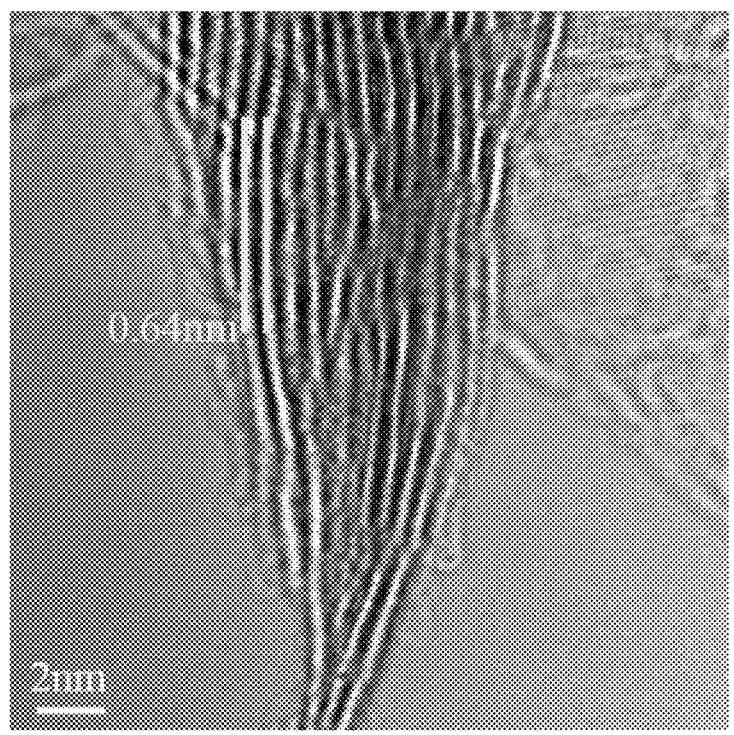
FIG. 5C is another TEM image of the molybdenum disulfide powder according to the first example of the present disclosure.

1. The first example: FIG. 5A are SEM images of the molybdenum disulfide powder according to the first example of the present disclosure, FIG. 5B is a TEM image of the molybdenum disulfide powder according to the first example of the present disclosure, and FIG. 5C is another TEM image of the molybdenum disulfide powder according to the first example of the present disclosure. In FIG. 5A, the larger image is observed at 10 k magnification, and the smaller image in the upper right corner is observed at 50 k magnification. FIG. 5B and FIG. 5C are observed at different magnifications. As shown in FIG. 5A, the molybdenum disulfide powder is formed in a nanoflower structure. The nanoflower structure is stacked from a plurality of layered structures in a random manner. Specifically, the nanoflower structure is stacked from a plurality of petals, and each of the petals is stacked from a plurality of layered structures. More specifically, the layered structure can be a single-layer structure or a multilayer structure. In FIG. 5A, the nanoflower structure is less obvious, and a diameter of the petal is about 0.1 μm. In FIG. 5C, it clearly shows that the molybdenum disulfide powder is a layer-stacked structure which is stacked from a plurality of layered structures. An Interlayer distance between the layered structures is about 0.64 nm.

Figure 6A:
FIG. 6A are SEM images of a molybdenum disulfide powder according to the second example of the present disclosure.
Figure 6B:
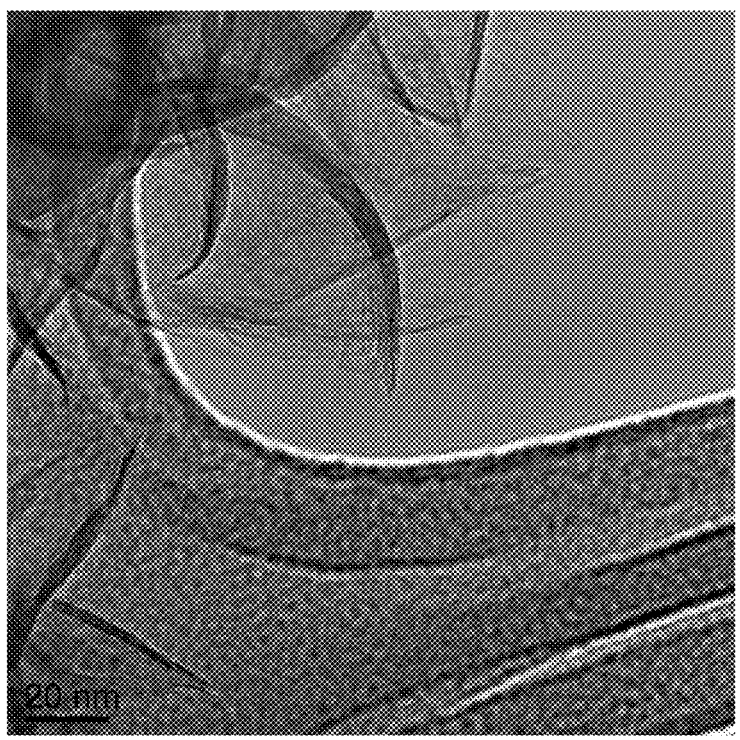
FIG. 6B is a TEM image of the molybdenum disulfide powder according to the second example of the present disclosure.
Figure 6C:
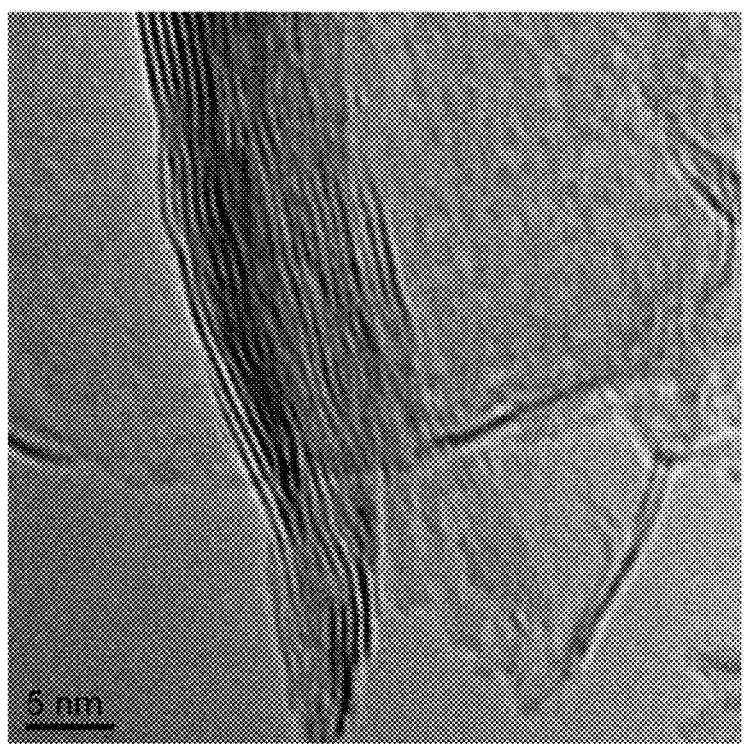
FIG. 6C is another TEM image of the molybdenum disulfide powder according to the second example of the present disclosure.
Figure 6D:
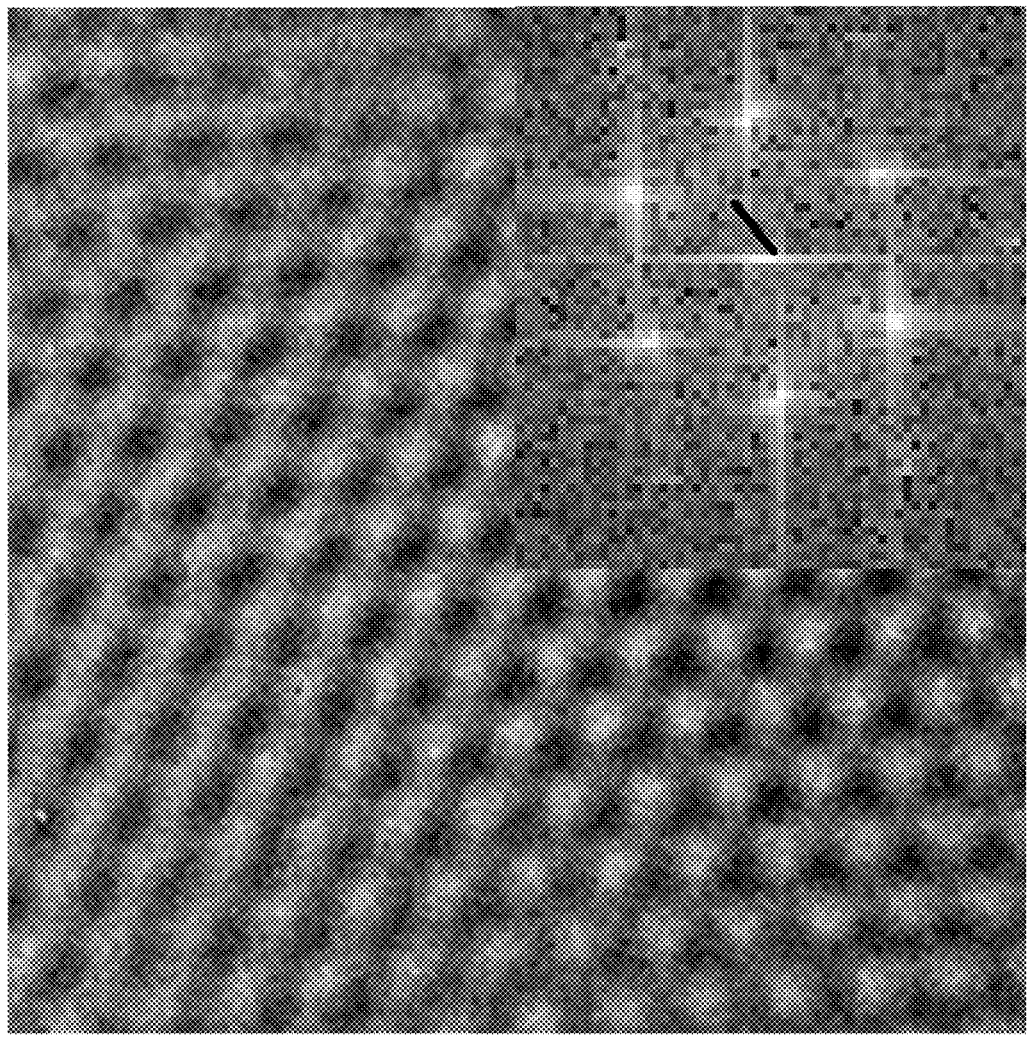
FIG. 6D is yet other TEM images of the molybdenum disulfide powder according to the second example of the present disclosure.

2. The second example: FIG. 6A are SEM images of the molybdenum disulfide powder according to the second example of the present disclosure, FIG. 6B is a TEM image of the molybdenum disulfide powder according to the second example of the present disclosure, FIG. 6C is another TEM image of the molybdenum disulfide powder according to the second example of the present disclosure, and FIG. 6D are yet other TEM images of the molybdenum disulfide powder according to the second example of the present disclosure. In FIG. 6A, the larger image is observed at 10 k magnification, and the smaller image in the upper right corner is observed at 50 k magnification. FIG. 6B, FIG. 6C and FIG. 6D are observed at different magnifications. The image in the upper right corner of FIG. 6D is a SAD pattern. As shown in FIG. 6A, the molybdenum disulfide powder is formed in a nanoflower structure. The nanoflower structure is stacked from a plurality of layered structures in a random manner. In FIG. 6A, the nanoflower structure is more obvious, a diameter of the nanoflower structure is about 1 μm, and a diameter of the petal is about 0.15 μm. In FIG. 6B and FIG. 6C, both clearly show that the molybdenum disulfide powder is a layer-stacked structure which is stacked from a plurality of layered structures. An Interlayer distance between the layered structures is about 0.64 nm. In FIG. 6D, there is no overlap between the images of atom, which can confirm that the molybdenum disulfide powder in FIG. 6D includes a single-layer structure (i.e., the layered structure which stacks and forms the petal of the nanoflower is a single-layer structure (i.e., the layered structure only has one layer)). In other words, the method according to the present disclosure can manufacture the molybdenum disulfide powder which includes at least one single-layer structure.

Figure 7A:
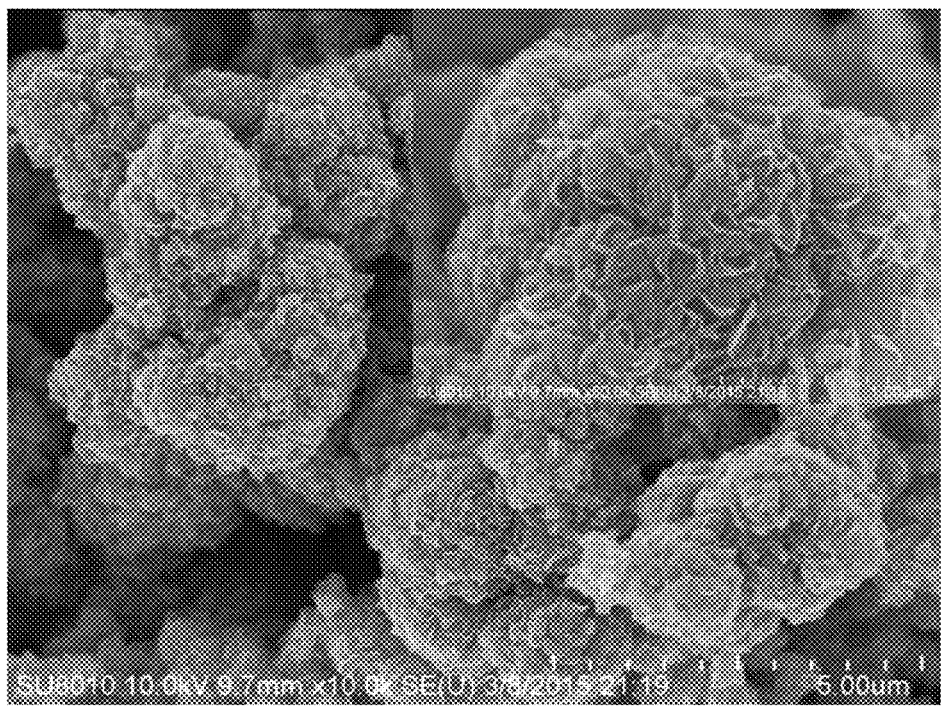
FIG. 7A are SEM images of a molybdenum disulfide powder according to the third example of the present disclosure.
Figure 7B:
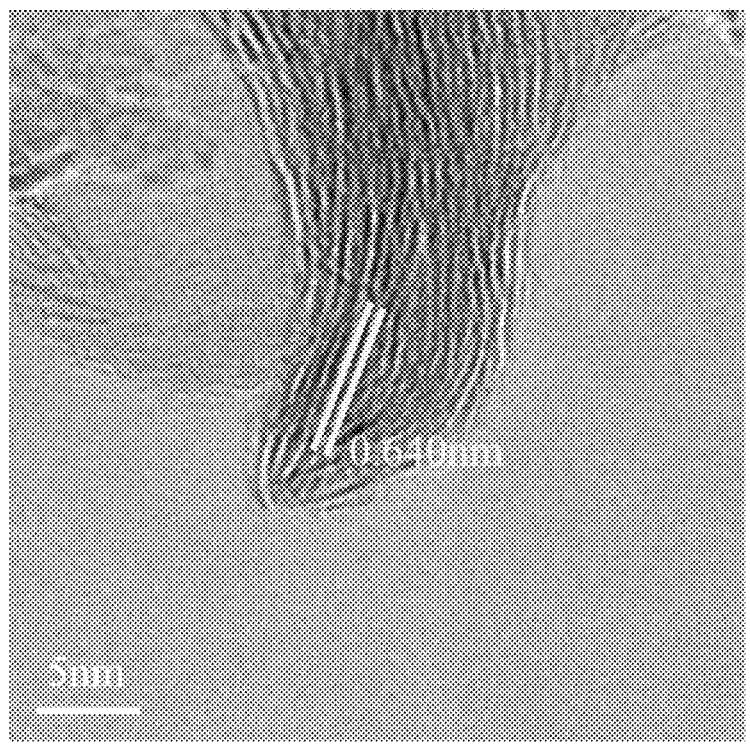
FIG. 7B is a TEM image of the molybdenum disulfide powder according to the third example of the present disclosure.

3. The third example: FIG. 7A are SEM images of the molybdenum disulfide powder according to the third example of the present disclosure, and FIG. 7B is a TEM image of the molybdenum disulfide powder according to the third example of the present disclosure. In FIG. 7A, the larger image is observed at 10 k magnification, and the smaller image in the upper right corner is observed at 50 k magnification. As shown in FIG. 7A, the molybdenum disulfide powder is formed in a nanoflower structure. The nanoflower structure is stacked from a plurality of layered structures in a random manner. In FIG. 7A, the nanoflower structure is obvious, a diameter of the nanoflower structure is about 1.5 μm, and a diameter of the petal is about 0.2 μm. In FIG. 7B, it clearly shows that the molybdenum disulfide powder is a layer-stacked structure which is stacked from a plurality of layered structures. An Interlayer distance between the layered structures is about 0.640 nm.

Figure 8A:
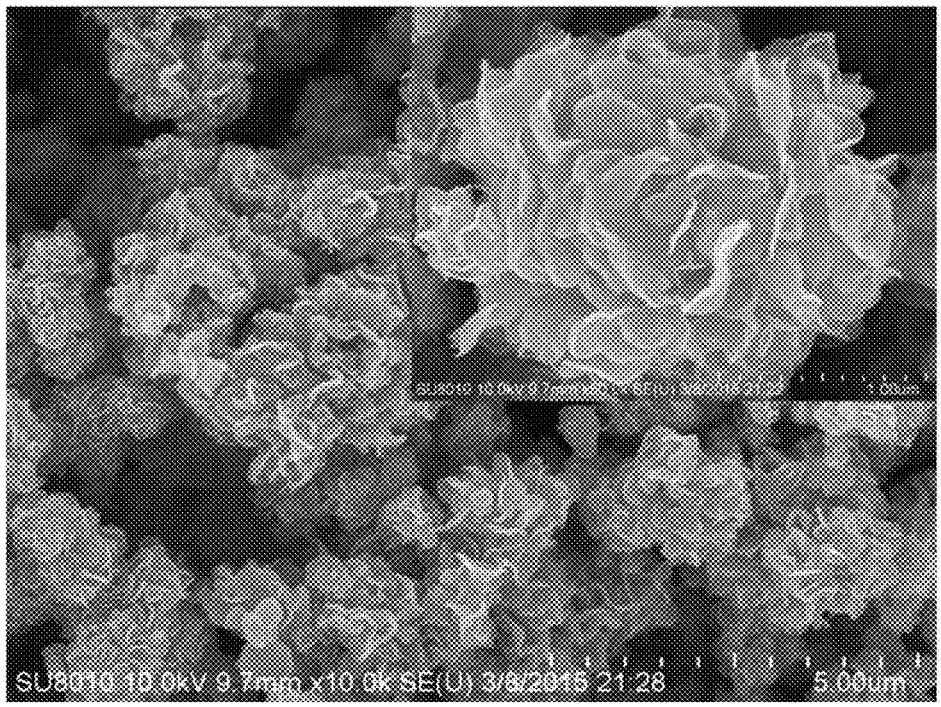
FIG. 8A are SEM images of a molybdenum disulfide powder according to the fourth example of the present disclosure.
Figure 8B:
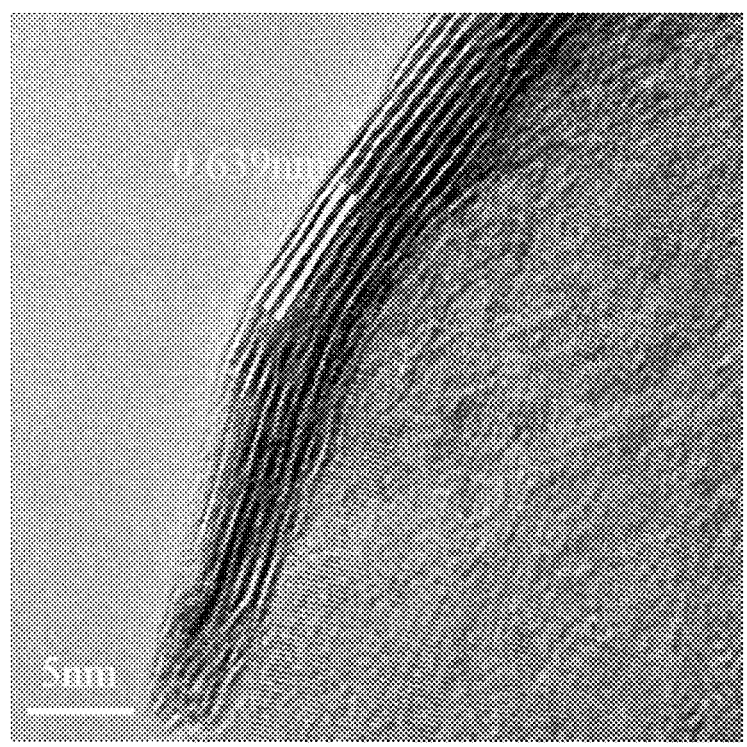
FIG. 8B is a TEM image of the molybdenum disulfide powder according to the fourth example of the present disclosure.

4. The fourth example: FIG. 8A are SEM images of the molybdenum disulfide powder according to the fourth example of the present disclosure, and FIG. 8B is a TEM image of the molybdenum disulfide powder according to the fourth example of the present disclosure. In FIG. 8A, the larger image is observed at 10 k magnification, and the smaller image in the upper right corner is observed at 50 k magnification. As shown in FIG. 8A, the molybdenum disulfide powder is formed in a nanoflower structure. The nanoflower structure is stacked from a plurality of layered structures in a random manner. In FIG. 8A, the nanoflower structure is obvious, a diameter of the nanoflower structure is about 2 μm, and a diameter of the petal is about 0.3 μm. In FIG. 8B, it clearly shows that the molybdenum disulfide powder is a layer-stacked structure which is stacked from a plurality of layered structures. An Interlayer distance between the layered structures is about 0.639 nm.

Figure 9A:
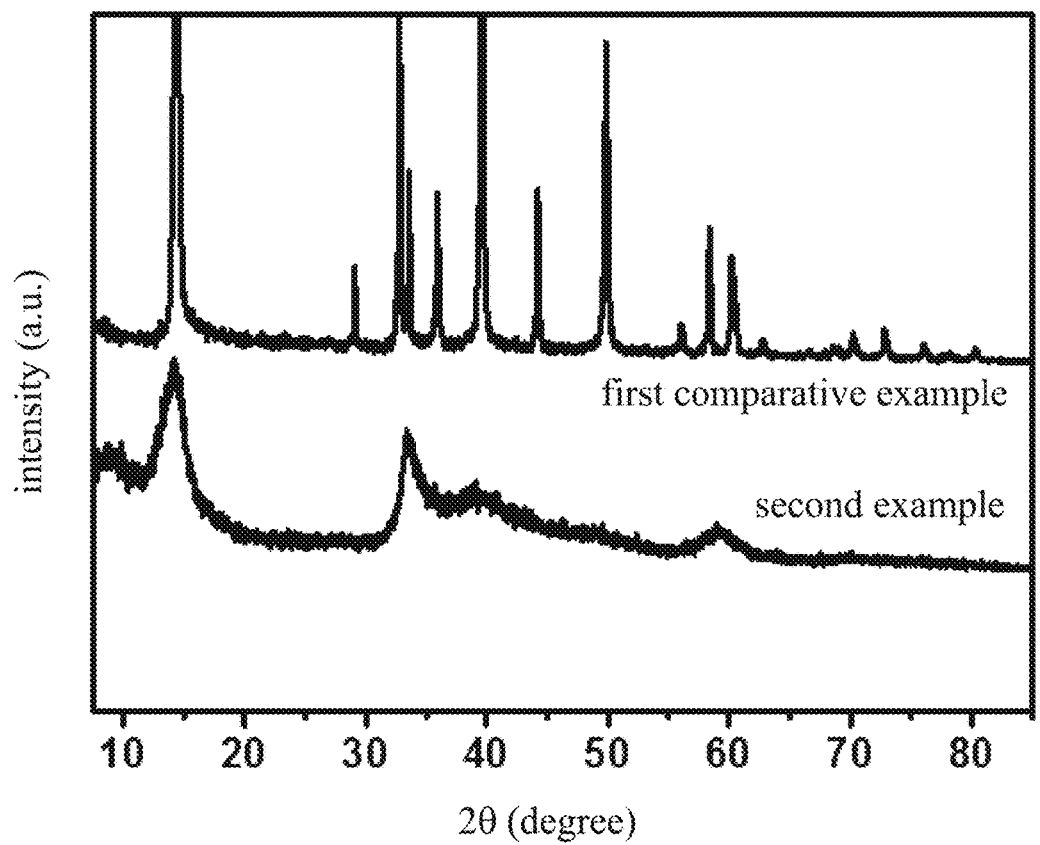
FIG. 9A shows X-Ray diffractometer (XRD) results of the molybdenum disulfide powders according to the second example of the present disclosure and the first comparative example.

Results of XRD. A XRD (Bruker D2 phaser) is used to analyze the structure of the molybdenum disulfide powder of the second example and the first comparative example. The measuring range of 2θ is 10° to 70°, the step size is 0.03°, and the scanning speed is 0.2°/sec. FIG. 9A shows XRD results of the molybdenum disulfide powders according to the second example of the present disclosure and the first comparative example, wherein the signal intensity of the first comparative example is not shown completely. As shown in FIG. 9A, the product of the second example is molybdenum disulfide powder. Moreover, the first comparative example shows strong crystalline property, which shows the first comparative example is a bulk material. The signal strength of the second example is much lower than that of the first comparative example, which shows the molybdenum disulfide powder of the second example includes a lot of layered structures with fewer layers or with only one layer.

Figure 9B:
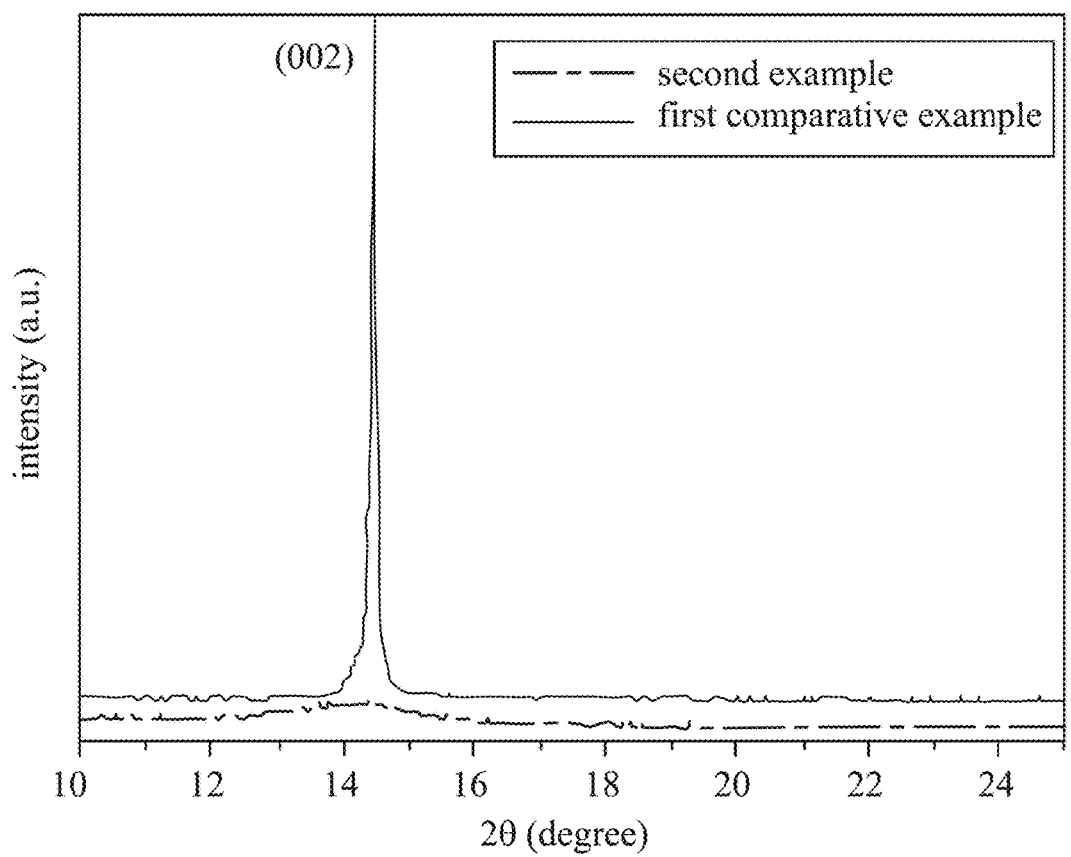
FIG. 9B shows other XRD results of the molybdenum disulfide powders according to the second example of the present disclosure and the first comparative example.

Please refer to FIG. 9B at the same time, which shows other XRD results of the molybdenum disulfide powder according to the second example of the present disclosure and the first comparative example. Specifically, FIG. 9B shows a partial measuring range of 2θ in FIG. 9A and shows the signal intensity of (002) plane more completely. The intensities represented by vertical axis in FIG. 9A and FIG. 9B are relative intensities. When the signal intensity of (002) plane of the first comparative example is shown more completely, the signal intensity of (002) plane of the second example is less obvious. As shown in FIG. 9B, the signal intensity of (002) plane of the first comparative example is much higher than that of the second example, which can further confirm that the molybdenum disulfide powder of the second example includes a lot of layered structures with fewer layers or with only one layer.

Figure 10:
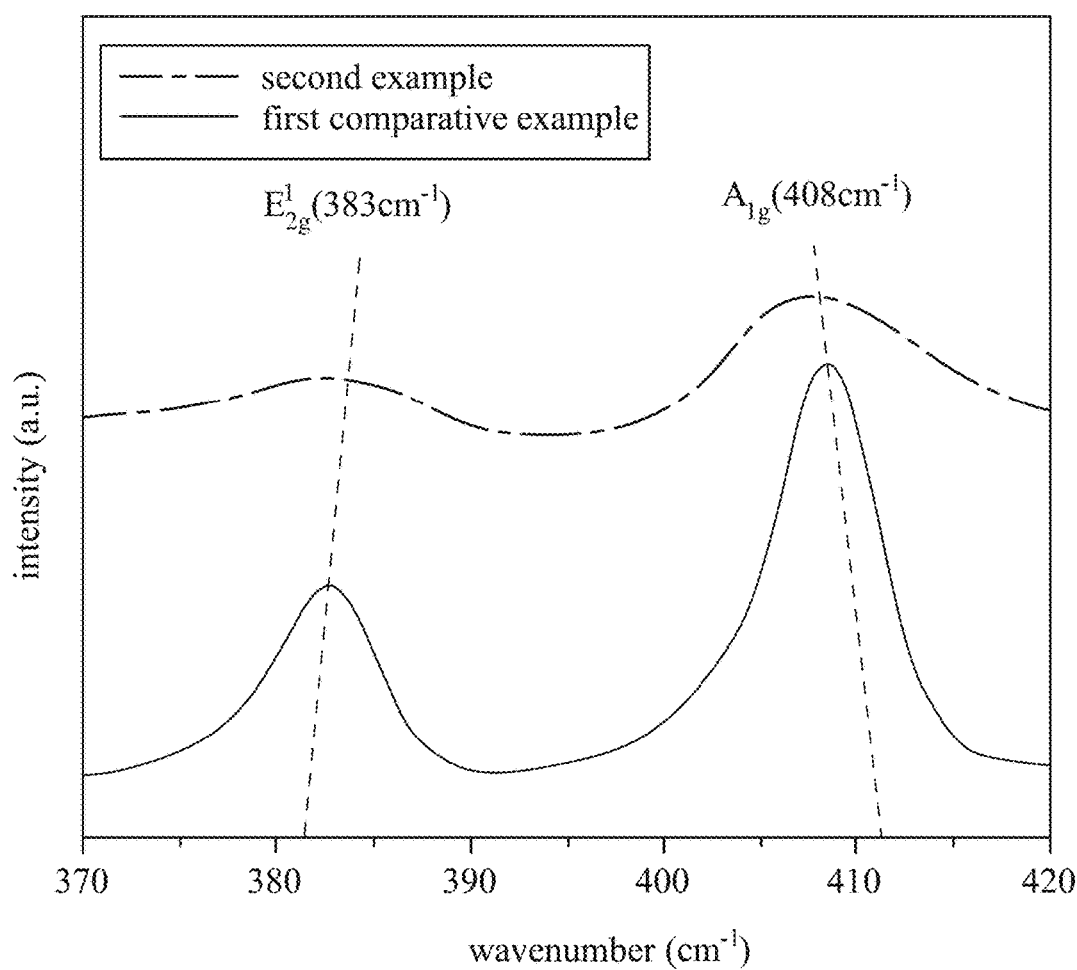
FIG. 10 shows Raman spectra of the molybdenum disulfide powders according to the second example of the present disclosure and the first comparative example.

Results of Raman spectrometer: a Raman spectrometer is used to analyze the vibration modes between atoms of the molybdenum disulfide powder according to the second example and the first comparative example, a 532 nm laser is used as the excitation laser, and the scanning range is set from 370 $cm^{-1}$ to 420 $cm^{-1}$. Please refer to FIG. 10, which shows Raman spectra of the molybdenum disulfide powders according to the second example of the present disclosure and the first comparative example. A Raman peak of a typical bulk material of molybdenum disulfide is at 383 $cm^{-1}$ and 408 $cm^{-1}$. As shown in FIG. 10, the molybdenum disulfide powder of the second example has a blue shift at 383 $cm^{-1}$ and a red shift at 408 $cm^{-1}$, which shows the layered structures of the molybdenum disulfide powder of the second example has fewer layers than that of the first comparative example. In other words, the method according to the present disclosure is favorable to manufacture the molybdenum disulfide powder stacked from the layered structures with fewer layers (i.e., the layered structures which stacks and forms the petals of the nanoflower have fewer layers).

Figure 11A:
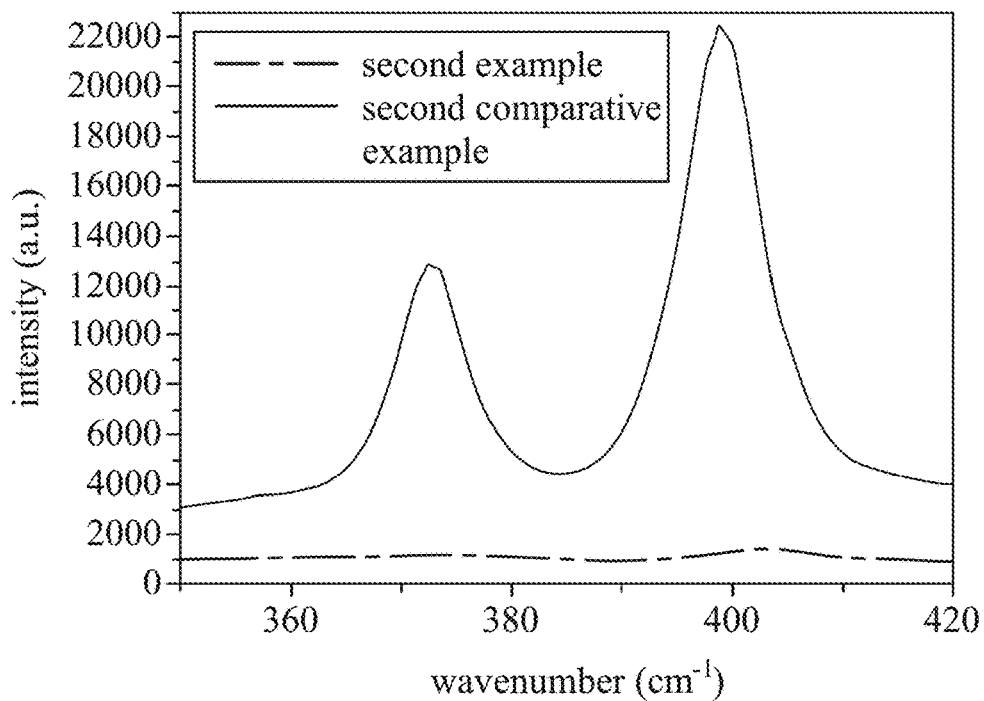
FIG. 11A shows Raman spectra of the molybdenum disulfide powders according to the second example of the present disclosure and the second comparative example.
Figure 11B:
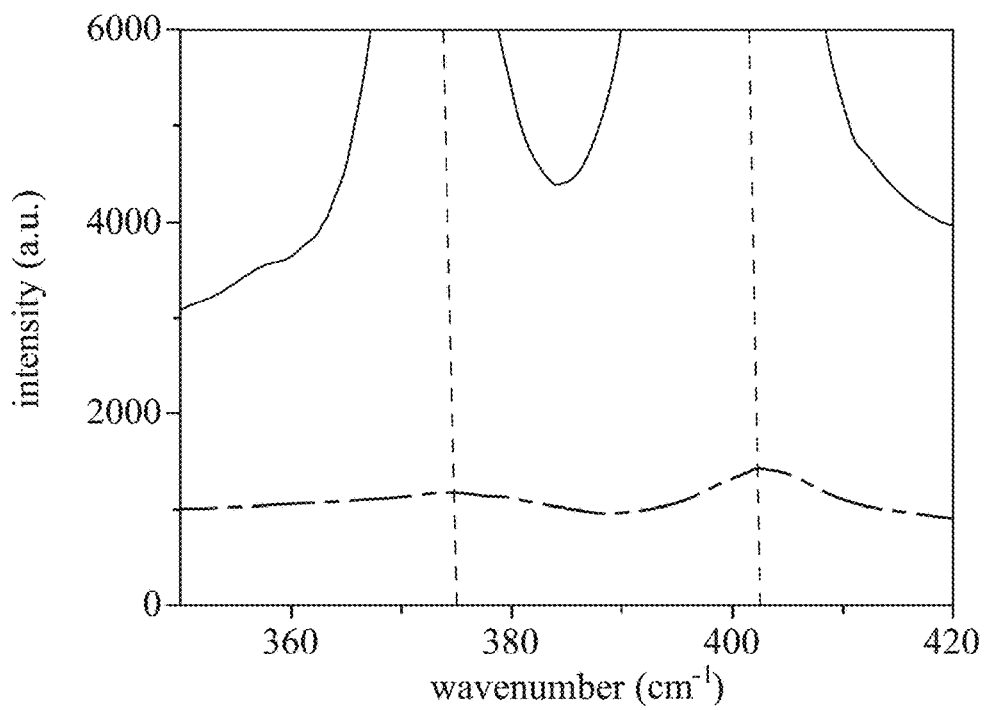
FIG. 11B is a partially enlarged view of FIG. 11A.

Please refer to FIG. 11A and FIG. 11B. FIG. 11A shows Raman spectra of the molybdenum disulfide powders according to the second example of the present disclosure and the second comparative example, and FIG. 11B is a partially enlarged view of FIG. 11A. As shown in FIG. 11A and FIG. 11B, the molybdenum disulfide powder of the second comparative example does not have a blue shift at 383 $cm^{-1}$ and a red shift at 408 $cm^{-1}$, which is different from the second example. It shows that when the titration method is changed, the molybdenum disulfide powder tends to agglomerate. Accordingly, it is unfavorable to form the molybdenum disulfide powder stacked from layered structures with fewer layers.

Results of specific surface area analysis: a surface area and porosimetry analyser (Micromeritics ASAP 2020) is used to measure the specific surface areas of the molybdenum disulfide powder of the first example to the fourth example. The specific surface areas of the first example to the fourth example are 69.21 $cm^2/g$, 52.64 $cm^2/g$, 35.28 $cm^2/g$ and 23.35 $cm^2/g$ in sequence. According to the results, it can be concluded that when the amount of $[BMIM]^+$ is increased, thicknesses of the petals of the nanoflowers are increased. Accordingly, the specific surface area is decreased.

Figure 12A:
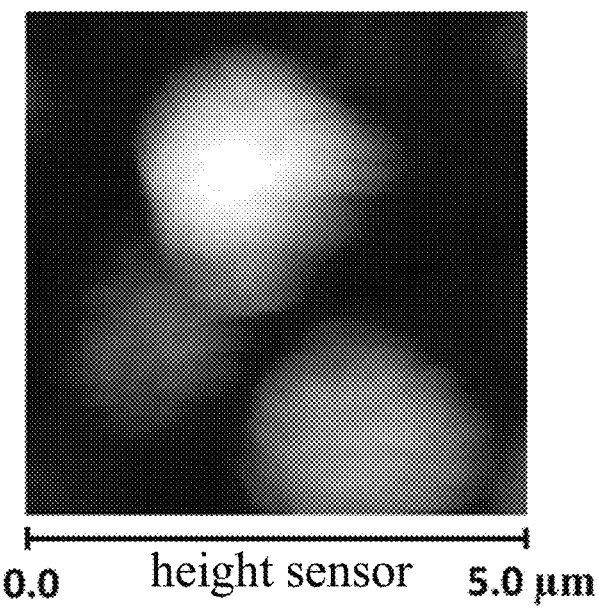
FIG. 12A is an atomic force microscope (AFM) image of the molybdenum disulfide powder according to the second example of the present disclosure.
Figure 12B:
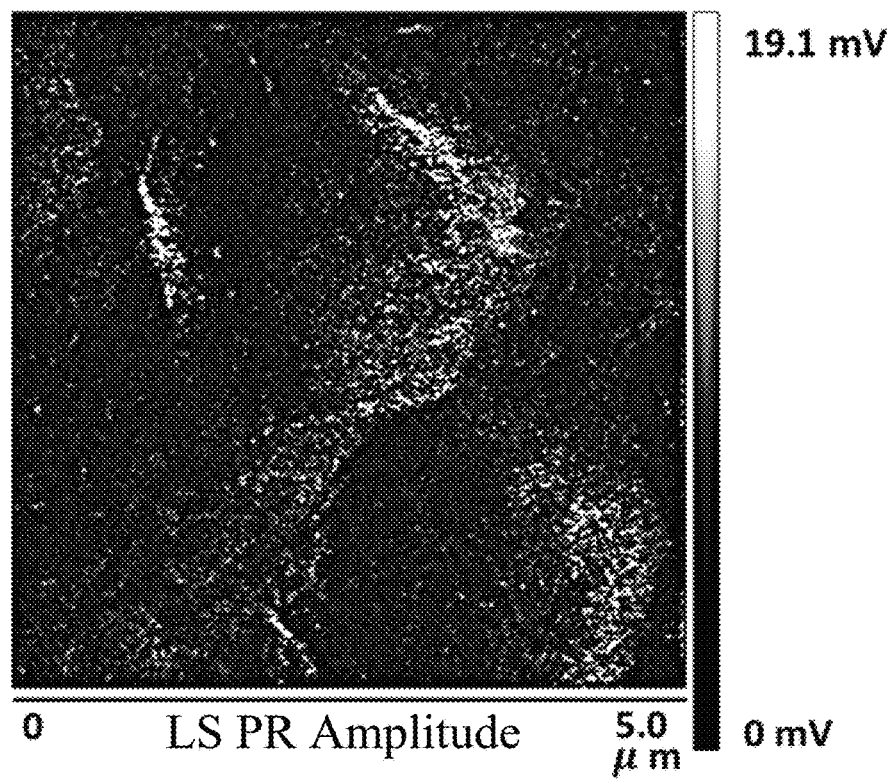
FIG. 12B shows a voltage potential distribution of FIG. 12A.
Figure 12C:
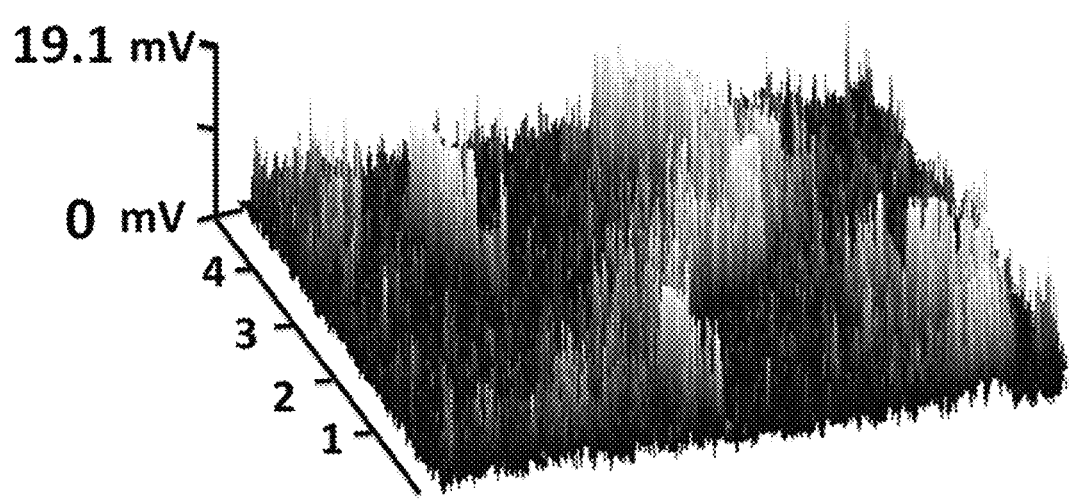
FIG. 12C is a three-dimensional (3D) view showing the voltage potential distribution of FIG. 12B.

Results of AFM: an AFM is used to observe the piezoelectric property of the molybdenum disulfide powder of the second example. Please refer to FIG. 12A to FIG. 12C. FIG. 12A is an AFM image of the molybdenum disulfide powder according to the second example of the present disclosure, FIG. 12B shows a voltage potential distribution of FIG. 12A, and FIG. 12C is a 3D view showing the voltage potential distribution of FIG. 12B. As shown in FIG. 12A to FIG. 12C, the molybdenum disulfide powder according to the present disclosure has different voltage potentials in the three dimensional directions. The voltage potentials can cause the separations of electrons and holes, which is favorable to enhance the catalytic activity of the molybdenum disulfide powder. It is apparent that the method according to the present disclosure is beneficial to manufacture the molybdenum disulfide powder stacked from the layered structures with odd layers, which features the molybdenum disulfide powder with piezoelectric property.

As shown in the foregoing results, the method according to the present disclosure is favorable to manufacture the molybdenum disulfide powder stacked from the layered structures with fewer layers. Also, the method according to the present disclosure is favorable to manufacture the molybdenum disulfide powder stacked from the layered structures with odd layers.

Method for Degrading an Organic Material

Figure 13:
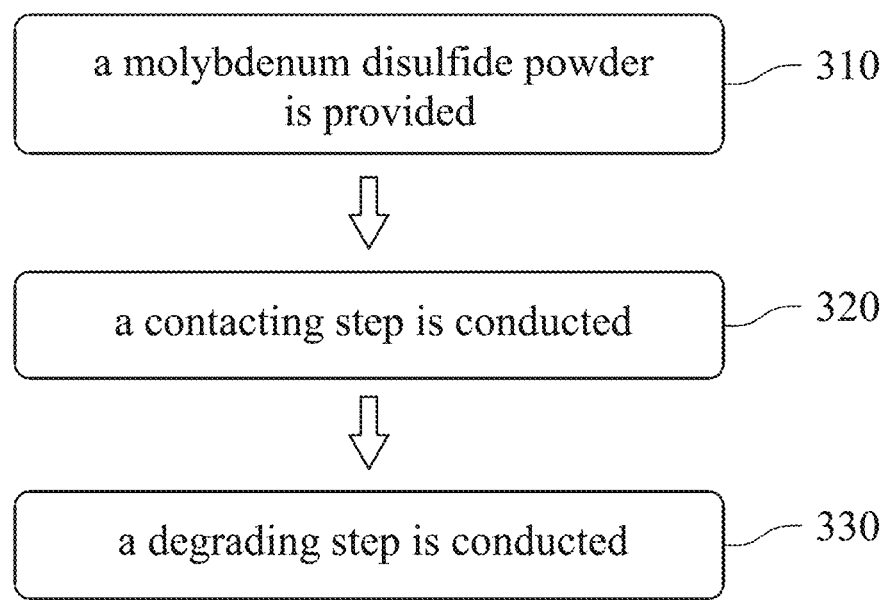
FIG. 13 is a flow diagram showing a method for degrading an organic material according to yet another embodiment of the present disclosure.

FIG. 13 is a flow diagram showing a method for degrading an organic material 300 according to yet another embodiment of the present disclosure. In FIG. 13, the method for degrading the organic material 300 includes Step 310, Step 320 and Step 330.

In Step 310, a molybdenum disulfide powder is provided, wherein the molybdenum disulfide powder is stacked from a plurality of layered structures, and at least one of the layered structures is an odd-layer structure. The molybdenum disulfide powder can be manufactured by the method according to the present disclosure (the method for manufacturing a molybdenum disulfide powder 100 and 200).

In Step 320, a contacting step is conducted, wherein the molybdenum disulfide powder is contacted with a medium, and the medium includes at least one organic material and water.

In Step 330, a degrading step is conducted, wherein a mechanical perturbation is generated in the medium to polarize the molybdenum disulfide powder, and a pair of electron and hole are generated for degrading the organic material.

Figure 14:
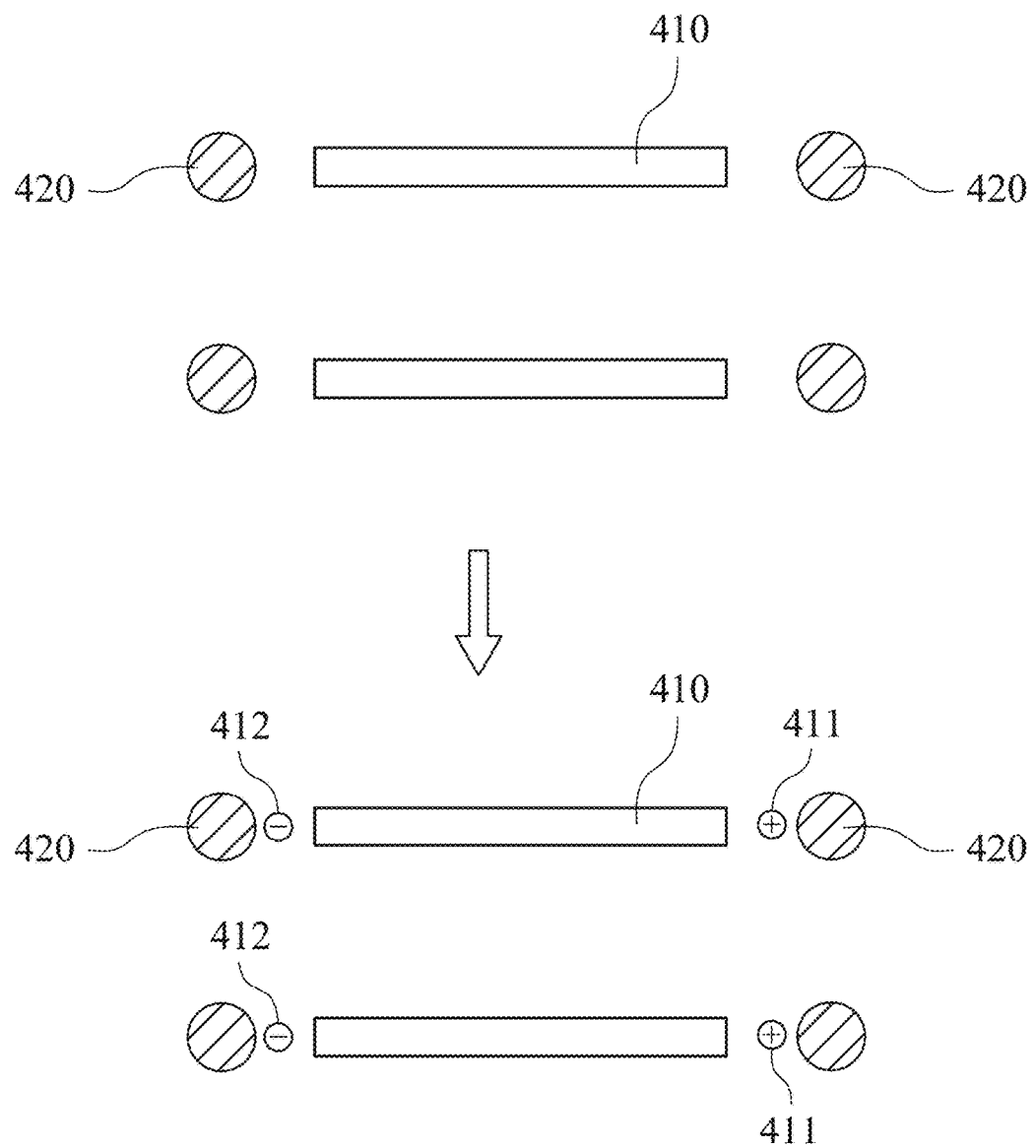
FIG. 14 is a schematic view showing a molybdenum disulfide powder in FIG. 13 degrading organic materials.

Please refer to FIG. 14 at the same time. FIG. 14 is a schematic view showing the molybdenum disulfide powder in FIG. 13 degrading organic materials. The molybdenum disulfide powder is a layer-stacked structure which is stacked from a plurality of layered structures 410. The molybdenum disulfide powder is contacted with a medium (not shown) which includes organic materials 420 and water (not shown). When a mechanical perturbation is generated in the medium, the mechanical perturbation is transmitted to the molybdenum disulfide powder to polarize the layered structures 410 thereof, and pairs of hole 411 and electron 412 are generated. The holes 411 have oxidation ability, and the electrons 412 have reduction ability. Moreover, the holes 411 can react with water molecules in the medium so as to generate hydroxyl radicals (not shown), hydrogen peroxide (not shown) or anions (not shown), so that the organic materials 420 can be degraded by redox reactions. Specifically, the molybdenum disulfide powder can be used to degrade organic materials in wastewater. In the application example, the medium is the aqueous solution formed from the wastewater. The molybdenum disulfide powder is added into the treatment channel of the wastewater, wherein the wastewater flows due to the different water pressures. The flow of the wastewater (includes partial vortexes and disturbances) can be viewed as the mechanical perturbation polarizing the molybdenum disulfide powder and causing the following redox reactions. Accordingly, the organic materials in the wastewater can be degraded so as to achieve a water purification effect. Alternatively, the molybdenum disulfide powder can be used to degrade organic gases in air. For example, the molybdenum disulfide powder can be coated on a filter of an air purifier. In the application example, the medium is the air. The air includes water vapor. When the air flows due to the different air pressures and goes through the filter coated with the molybdenum disulfide powder, the flow of the air (includes partial vortexes and disturbances) can be viewed as the mechanical perturbation. The mechanical perturbation can polarize the molybdenum disulfide powder so as to generate an inner electric field and form the pairs of electron and hole, and cause the following redox reactions. Accordingly, the organic gases in the air can be degraded so as to achieve a deodorization effect and an air purification effect.

Figure 15:
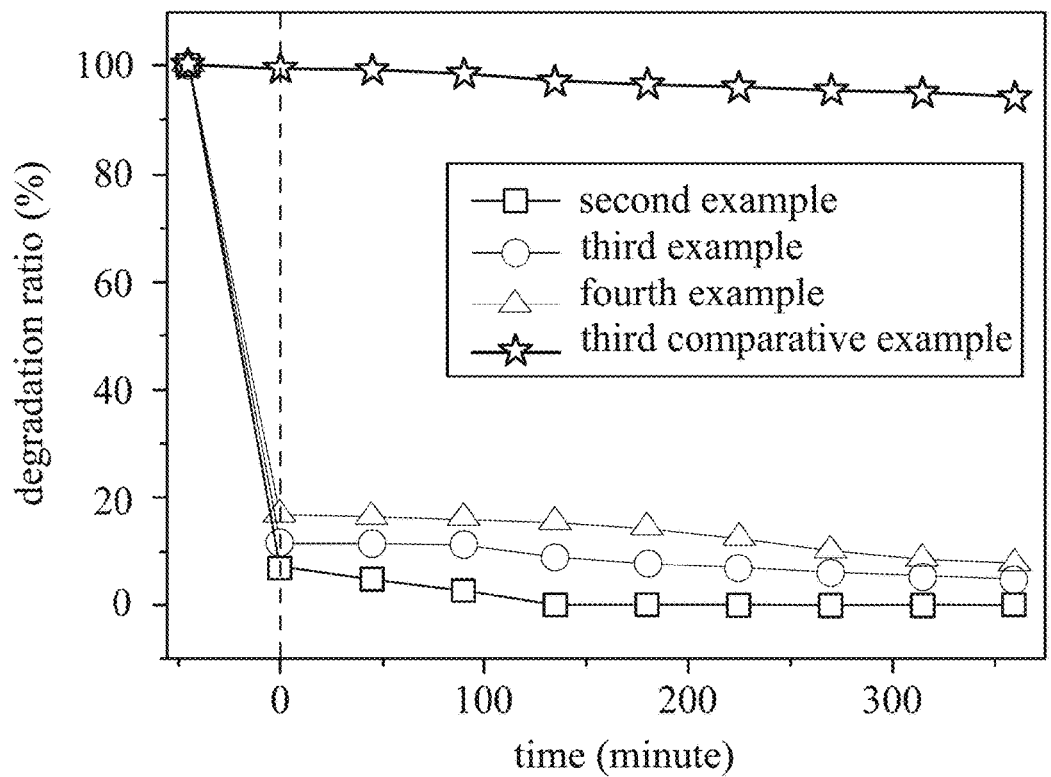
FIG. 15 shows relationships between a degradation ratio for rhodamine and time of the second example to the fourth example according to the present disclosure and the third comparative example.

FIG. 15 shows relationships between a degradation ratio for rhodamine and time of the second example to the fourth example according to the present disclosure and the third comparative example. The relationships of FIG. 15 are obtained as follows. The molybdenum disulfide powders (5 mg) of the second example to the fourth example are added into a rhodamine solution (40 ml, 10 ppm), respectively. The third comparative example is a rhodamine solution (40 ml, 10 ppm) without adding a molybdenum disulfide powder. The four rhodamine solutions of the second example to the fourth example and the third comparative example are put into a closed catalytic reaction container which can block lights, and applied with an ultrasonic wave of 40 kHz for 50 minutes, then the degradation ratios for rhodamine of the four rhodamine solutions are measured. Afterwards, the four rhodamine solutions are taken outside the closed catalytic reaction container and irradiated with a xenon lamp, and the degradation ratios for rhodamine of the four rhodamine solutions are measured every 50 minutes. The degradation ratios for rhodamine are plotted with time so as to obtain FIG. 15. In FIG. 15, the time before 0 minute represents that the four rhodamine solutions are put in the closed catalytic reaction container and applied with the ultrasonic wave. The time after 0 minute represents that the four rhodamine solutions are taken outside the closed catalytic reaction container and irradiated with the xenon lamp. As shown in FIG. 15, under the condition of applying the ultrasonic wave in darkness or under the condition of irradiating with the xenon lamp, there almost no degradation occurs in the rhodamine solution of the third comparative example which is not added with the molybdenum disulfide powder. However, the rhodamine solutions of the second example to the fourth example under the condition of applying the ultrasonic wave in darkness, the degradations ratio for rhodamine can be under 20%. It is obvious that the catalytic activity of the molybdenum disulfide powder according to the present disclosure can be induced by an external force (which is a kind of mechanical perturbation) and does not need to irradiate with lights or rely on the irradiation of lights with short wavelength. Accordingly, it is favorable to reduce the energy consumption. In other words, the degradation reactions caused by the molybdenum disulfide powder according to the present disclosure can even conduct in darkness, i.e., the degradation reactions caused by the molybdenum disulfide powder can conduct at nights, which is unrestricted by time in practical application. Accordingly, it is favorable to broaden the application of the molybdenum disulfide powder according to the present disclosure.

Figure 16A:
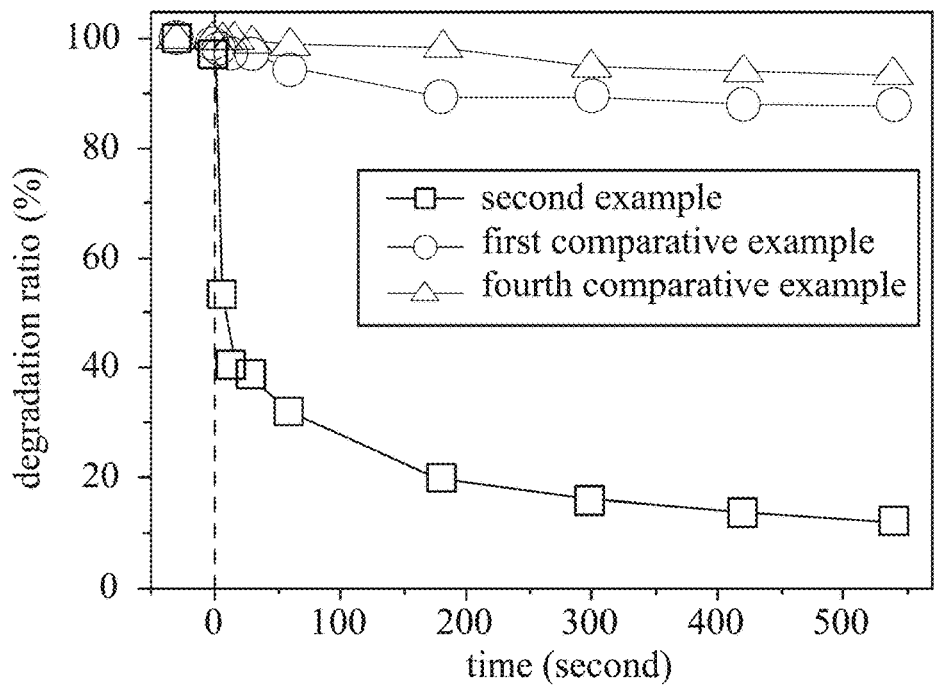
FIG. 16A shows relationships between the degradation ratio for rhodamine and time of the second example according to the present disclosure, the first comparative example and the fourth comparative example.

FIG. 16A shows relationships between the degradation ratio for rhodamine and time of the second example according to the present disclosure, the first comparative example and the fourth comparative example. The relationships of FIG. 16A are obtained as follows. The molybdenum disulfide powders (5 mg) of the second example and the first comparative example, and the titanium dioxide powder (5 mg) of the fourth comparative example are added into three rhodamine solutions (40 ml, 10 ppm), respectively. The three rhodamine solutions are put into a closed catalytic reaction container which can block lights and stand still for a while, then the degradation ratios for rhodamine are measured and recorded. Afterward, the catalytic reaction container is applied with an ultrasonic wave of 40 kHz, then the degradation ratios for rhodamine are measured. The degradation ratios for rhodamine are plotted with time so as to obtain FIG. 16A. In FIG. 16A, the time before 0 minute represents that the three rhodamine solutions are put in the closed catalytic reaction container and stand still. The time after 0 minute represents that the three rhodamine solutions are applied with the ultrasonic wave. As shown in FIG. 16A, the catalytic activity of the molybdenum disulfide powder according to the present disclosure can be induced by an external force (which is a kind of mechanical perturbation) and does not need to irradiate with lights or rely on the irradiation of lights with short wavelength. Accordingly, the molybdenum disulfide powder according to the present can rapidly degrade organic material (rhodamine in this case).

Figure 16B:
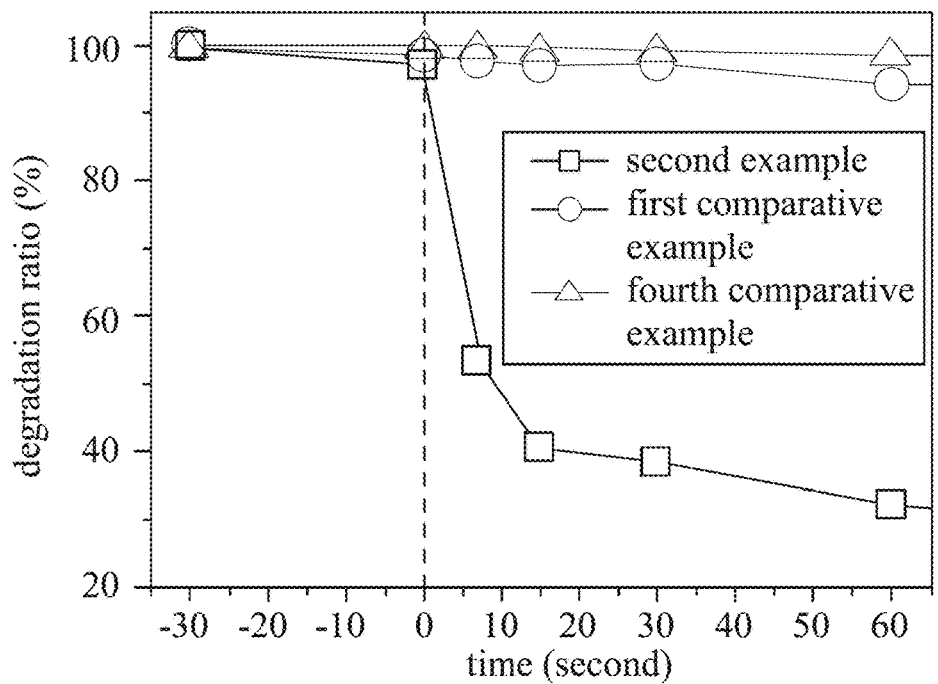
FIG. 16B is a partially enlarged view of FIG. 16A.

Please further refer to FIG. 16B, which is a partially enlarged view of FIG. 16A. Specifically, FIG. 16B shows the 30 seconds before applying the ultrasonic wave and the 60 seconds after applying the ultrasonic wave in FIG. 16A. As shown in FIG. 16B, when no ultrasonic wave is applied, the degradation effect of the second example is the best, but the difference between the degradation effects of the second example, the first comparative example and the fourth comparative example is not significant. However, when the ultrasonic wave is applied, the degradation ratio for rhodamine of the second example can be under 50% within 10 seconds, but the degradation ratios for rhodamine of the first comparative example and the fourth comparative example do not decline significantly. In other words, when only the external force is provided in darkness (i.e. no irradiation of lights is provided), the degradation efficiency of the commercially available photocatalysts, such as the first comparative example and the fourth comparative example, are far less than that of the molybdenum disulfide powder according to present disclosure. As shown in FIG. 16A and FIG. 16B, the method according to the present disclosure (the method for manufacturing a molybdenum disulfide powder 100 and 200) is favorable to manufacturing the molybdenum disulfide powder stacked from layered structures with high density of odd layers.

Figure 17A:
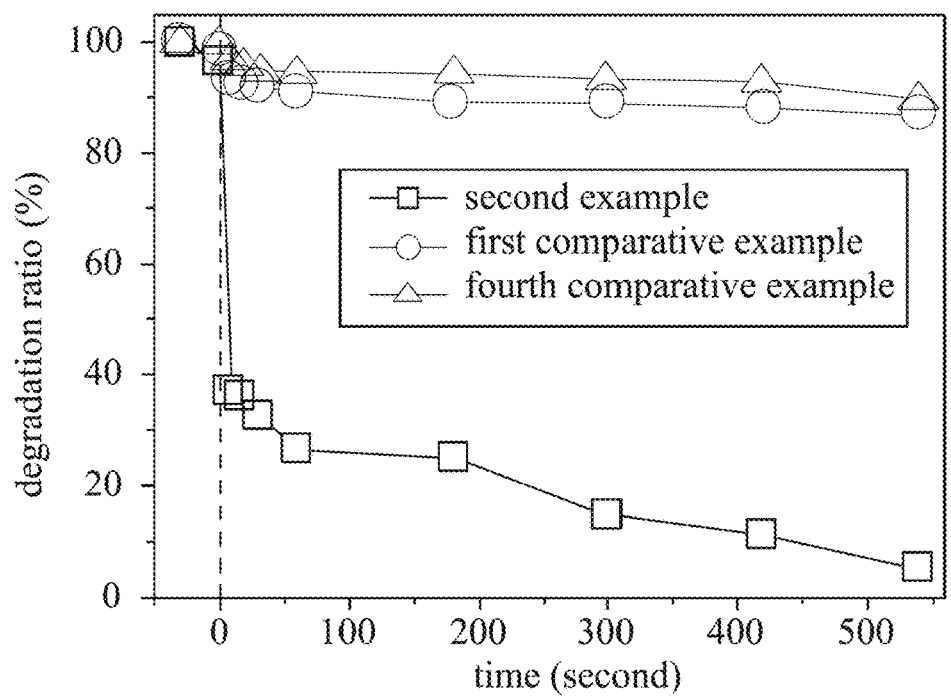
FIG. 17A shows other relationships between the degradation ratio for rhodamine and time of the second example according to the present disclosure, the first comparative example and the fourth comparative example.

FIG. 17A shows other relationships between the degradation ratio for rhodamine and time of the second example according to the present disclosure, the first comparative example and the fourth comparative example. Comparing FIG. 17A to FIG. 16A, a xenon lamp is provided during the whole degradation process in FIG. 17A. That is, the time before 0 minute represents that the three rhodamine solutions are irradiated with the xenon lamp and stand still. The time after 0 minute represents that the three rhodamine solutions are applied with the ultrasonic wave and irradiated with the xenon lamp simultaneously. Comparing FIG. 17A to FIG. 16A, it shows that the irradiation of the xenon lamp can further enhance the degradation efficiency.

Figure 17B:
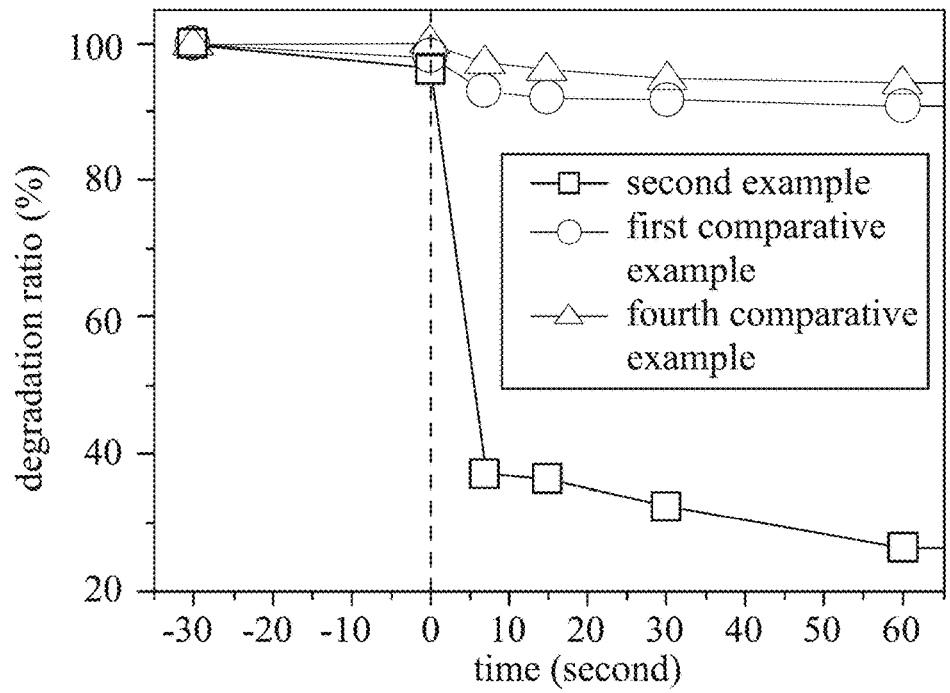
FIG. 17B is a partially enlarged view of FIG. 17A.

Please further refer to FIG. 17B, which is a partially enlarged view of FIG. 17A. Specifically, FIG. 17B shows the 30 seconds before applying the ultrasonic wave and the 60 seconds after applying the ultrasonic wave in FIG. 17A. As shown in FIG. 17B, when the irradiation of the xenon lamp and the ultrasonic wave are simultaneously applied, the degradation ratio for rhodamine of the second example can be under 40% within 10 seconds, but the degradation ratios for rhodamine of the first comparative example and the fourth comparative example cannot decline to 90%. In other words, when the irradiation of the xenon lamp and the external force are simultaneously applied, the degradation efficiency of the commercially available photocatalysts, such as the first comparative example and the fourth comparative example, are far less than that of the molybdenum disulfide powder according to present disclosure. As shown in FIG. 17A and FIG. 17B, the method according to the present disclosure (the method for manufacturing a molybdenum disulfide powder 100 and 200) is favorable to manufacturing the molybdenum disulfide powder stacked from layered structures with odd layers.

Figure 18:
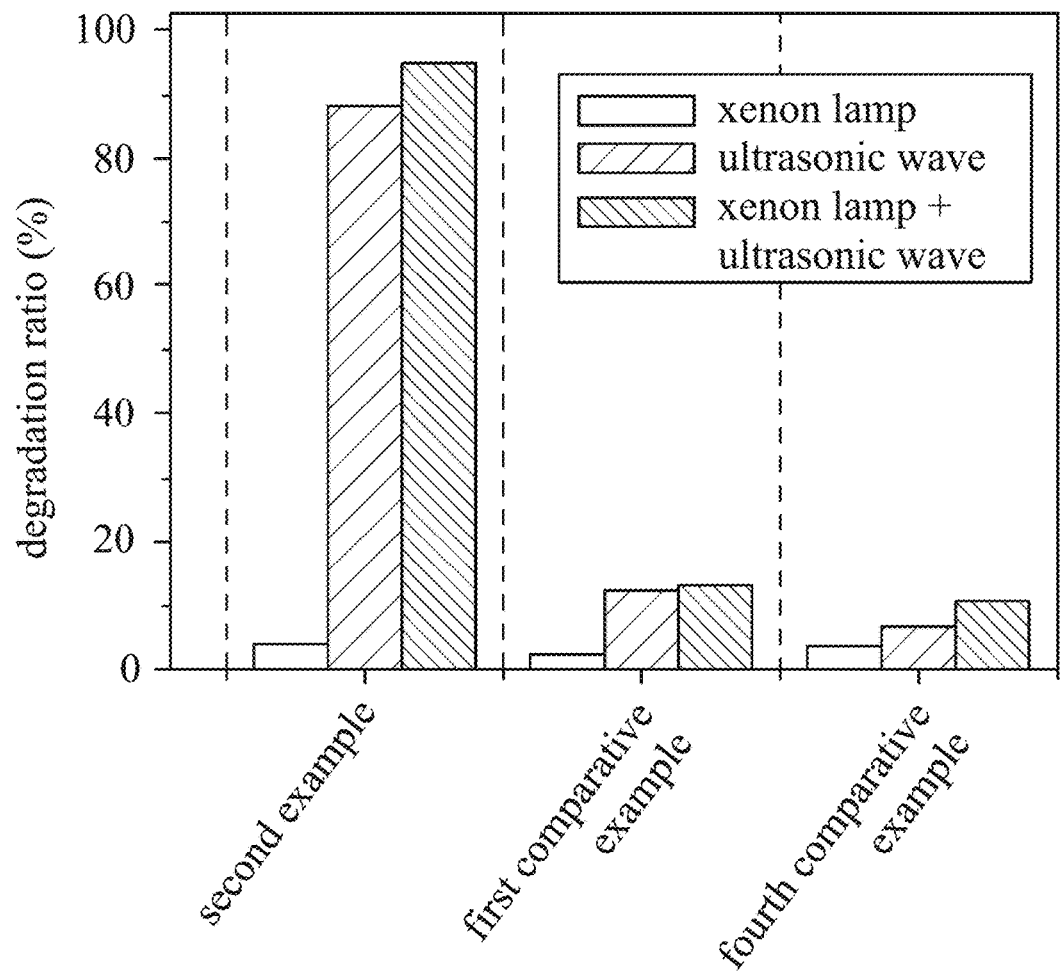
FIG. 18 is a comparison chart comparing the degradation ratios for rhodamine of the second example according to the present disclosure, the first comparative example and the fourth comparative example.

FIG. 18 is a comparison chart comparing the degradation ratios for rhodamine of the second example according to the present disclosure, the first comparative example and the fourth comparative example. As shown in FIG. 18, when the molybdenum disulfide powder according to the present disclosure is only irradiated with the xenon lamp, a degrading ability comparable to the commercial available titanium dioxide can be provided. When the molybdenum disulfide powder according to the present disclosure is only applied with the ultrasonic wave, a degrading ability superior to the commercial available molybdenum disulfide and the commercial available titanium dioxide can be provided. When the molybdenum disulfide powder according to the present disclosure is irradiated with the xenon lamp and applied with the ultrasonic wave simultaneously, the degrading ability thereof can be further enhanced.

As shown in FIG. 15 to FIG. 18, as for the conventional photocatalysts, the desired catalytic activity only can be provided when irradiated with lights or irradiated with lights having short wavelength. However, as for the molybdenum disulfide powder according to the present disclosure, the catalytic activity thereof can be induced by an external force, such as the mechanical perturbation generated in the medium (which can be provided by the ultrasonic wave), and without irradiating with lights. Accordingly, the energy consumption can be reduced significantly.

Figure 19:
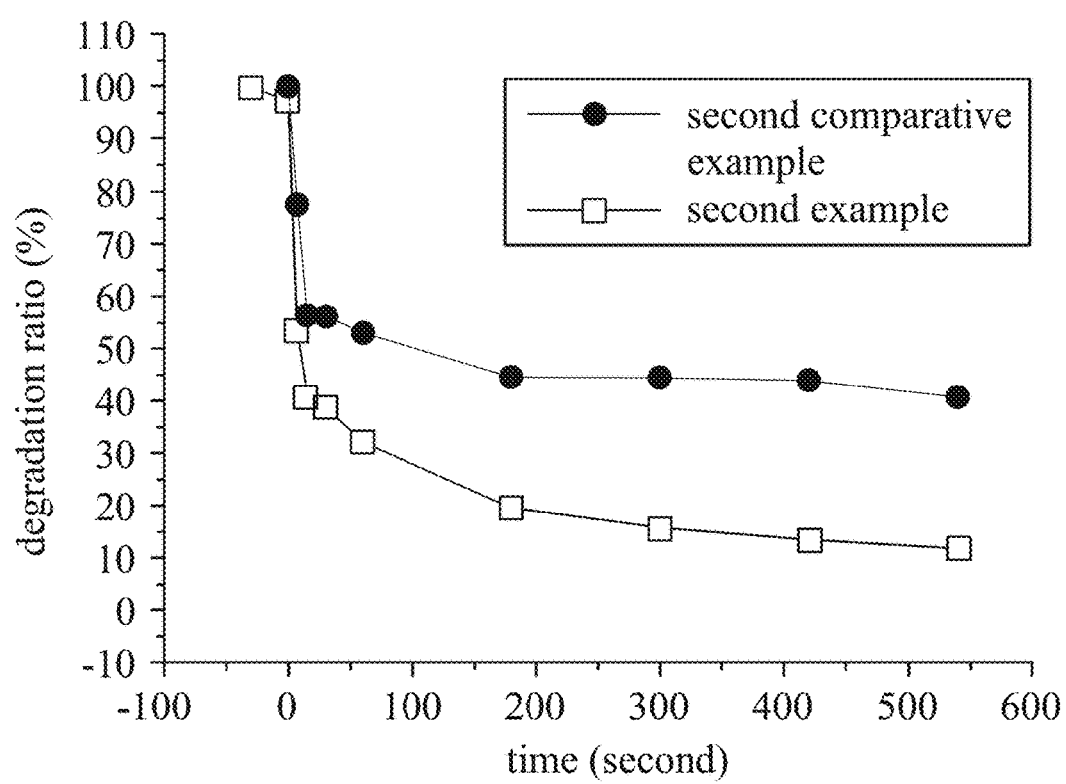
FIG. 19 shows relationships between a degradation ratio for rhodamine and time of the second example according to the present disclosure and the second comparative example.

FIG. 19 shows relationships between a degradation ratio for rhodamine and time of the second example according to the present disclosure and the second comparative example. The relationships of FIG. 19 are obtained as follows. The molybdenum disulfide powders (5 mg) of the second example and the second comparative example are added into two rhodamine solutions (40 ml, 10 ppm), respectively. The two rhodamine solutions are put into a closed catalytic reaction container which can block lights and stand still for a while, and the degradation ratios for rhodamine are measured and recorded. Afterward, the catalytic reaction container is applied with an ultrasonic wave of 40 kHz, then the degradation ratios for rhodamine are measured. The degradation ratios for rhodamine are plotted with time so as to obtain FIG. 19. In FIG. 19, the time before 0 minute represents that the two rhodamine solutions are put in the closed catalytic reaction container and stand still. The time after 0 minute represents that the two rhodamine solutions are applied with the ultrasonic wave. As shown in FIG. 19, the degradation efficiency of the second example is better than that of the second comparative example, which shows that when manufacturing the molybdenum disulfide powder, the titrating rate of the acid solution is slower, and the molybdenum disulfide powder stacked from layered structures with fewer layers can be favorably formed.

Method for Sterilizing

Figure 20:
FIG. 20 is a flow diagram showing a method for sterilizing according to yet another embodiment of the present disclosure.
Figure 20:

FIG. 20 is a flow diagram showing a method for sterilizing 500 according to yet another embodiment of the present disclosure. In FIG. 20, the method for sterilizing 500 includes Step 510, Step 520 and Step 530.

In Step 510, a molybdenum disulfide powder is provided. The molybdenum disulfide powder is stacked from a plurality of layered structures, and at least one of the layered structures is an odd-layer structure. The molybdenum disulfide powder can be manufactured by the method according to the present disclosure (the method for manufacturing a molybdenum disulfide powder 100 and 200).

In Step 520, a contacting step is conducted, wherein the molybdenum disulfide powder is contacted with a medium, and the medium includes at least one bacterium and a water.

In Step 530, a sterilizing step is conducted, wherein a mechanical perturbation is generated in the medium to polarize the molybdenum disulfide powder, and a pair of electron and hole are generated for killing the bacterium. The schematic view showing the pairs of electron and hole generated from the molybdenum disulfide powder can refer to FIG. 14. With the redox ability provided by the pair of electron and hole, the cell membrane of the bacterium can be spoiled so as to achieve a sterilizing effect. The medium can be an aqueous solution or an air. That is, the molybdenum disulfide powder according to the present disclosure can be applied to kill the bacteria in aqueous solution or in air. The bacteria can be but is not limited to mildew, *Escherichia coli*, *Pseudomonas aeruginosa*, *Staphylococcus*, Pyogenic bacteria and *Trichophyton*.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:
1. A method for degrading an organic material, comprising:
providing a molybdenum disulfide powder, wherein the molybdenum disulfide powder is stacked from a plurality of layered structures, and at least one of the layered structures is an odd-layer structure;

conducting a contacting step, wherein the molybdenum disulfide powder is contacted with a medium, and the medium comprises at least one organic material and water; and conducting a degrading step, wherein a mechanical perturbation is generated in the medium to polarize the molybdenum disulfide powder, and a pair of electron and hole are generated for degrading the organic material.

2. The method for degrading the organic material of claim 1, wherein the medium is an aqueous solution.

3. The method for degrading the organic material of claim 2, wherein the organic material is rhodamine or methylene blue.

4. The method for degrading the organic material of claim 2, wherein the mechanical perturbation is generated by an ultrasonic wave.

5. The method for degrading the organic material of claim 1, wherein the medium is an air.

6. The method for degrading the organic material of claim 5, wherein the organic material is an organic gas.

7. A method for sterilizing, comprising:

providing a molybdenum disulfide powder, wherein the molybdenum disulfide powder is stacked from a plurality of layered structures, and at least one of the layered structures is an odd-layer structure;

conducting a contacting step, wherein the molybdenum disulfide powder is contacted with a medium, and the medium comprises at least one bacterium and water; and conducting a sterilizing step, wherein a mechanical perturbation is generated in the medium to polarize the molybdenum disulfide powder, and a pair of electron and hole are generated for killing the bacterium.

8. The method for sterilizing of claim 7, wherein the medium is an air or an aqueous solution.

* * * * *